US009474533B2

(12) United States Patent
Mathis et al.

(10) Patent No.: US 9,474,533 B2
(45) Date of Patent: Oct. 25, 2016

(54) CROSS-SECTIONAL MODIFICATION DURING DEPLOYMENT OF AN ELONGATE LUNG VOLUME REDUCTION DEVICE

(71) Applicant: PneumRx, Inc., Mountain View, CA (US)

(72) Inventors: Mark L. Mathis, Fremont, CA (US); Patrick Wu, Pleasanton, CA (US); David Lehrberg, Mountain View, CA (US); Jaime Vasquez, Fremont, CA (US); Erin McGurk, Mountain View, CA (US); Ronald Dieck, Mountain View, CA (US); Andrew Stein, Mountain View, CA (US)

(73) Assignee: PneumRx, Inc., Mountain View, CA (US)

(*) Notice: Subject to any disclaimer, the term of this patent is extended or adjusted under 35 U.S.C. 154(b) by 0 days.

(21) Appl. No.: 14/225,892

(22) Filed: Mar. 26, 2014

(65) Prior Publication Data
US 2015/0073563 A1    Mar. 12, 2015

Related U.S. Application Data

(62) Division of application No. 12/782,515, filed on May 18, 2010, now Pat. No. 8,721,734.

(60) Provisional application No. 61/179,306, filed on May 18, 2009.

(51) Int. Cl.
*A61F 2/04* (2013.01)
*A61B 17/12* (2006.01)
(Continued)

(52) U.S. Cl.
CPC ....... *A61B 17/12104* (2013.01); *A61B 1/2676* (2013.01); *A61B 17/10* (2013.01);
(Continued)

(58) Field of Classification Search
CPC ............ A61B 17/10; A61B 17/12022; A61B 17/12031; A61B 17/12104; A61B 17/1214; A61B 17/12145; A61B 17/1215; A61B 17/12168; A61B 17/12172
See application file for complete search history.

(56) References Cited

U.S. PATENT DOCUMENTS 3,559,652 A   2/1971 Banitt et al.
4,013,080 A   3/1977 Froning
(Continued)

FOREIGN PATENT DOCUMENTS

CN   2756175      2/2006
CN   1753703 A    3/2006
(Continued)

OTHER PUBLICATIONS

U.S. Appl. No. 14/260,644, filed Apr. 24, 2014 by Mathis et al. (Unpublished.).
(Continued)

*Primary Examiner* — Julie A Szpira
(74) *Attorney, Agent, or Firm* — Kilpatrick Townsend and Stockton LLP

(57) ABSTRACT

Elongate implant structures can be introduced into an airway system to a target airway axial region, often to apply lateral bending and/or compression forces against the lung tissue from within the airways for an extended period of time. Structures or features of the implants may inhibit tissue reactions that might otherwise allow portions of the device to eventually traverse through the wall of the airway. The devices may enhance the area bearing laterally on the tissue of a surrounding airway lumen wall. Embodiments may have features which increase the device friction with the airway to allow the device to grip the surrounding airway as the device is deployed. An appropriate adhesive may be introduced around the device in the lung. Hydrophilic material may inhibit biofilm formation, or features which induce some tissue ingrowth (stimulation of tissue growth) may enhance implanted device supported.

19 Claims, 32 Drawing Sheets

(51) Int. Cl.
*A61B 1/267* (2006.01)
*A61B 17/10* (2006.01)
*A61B 17/00* (2006.01)

(52) U.S. Cl.
CPC ....... *A61B17/1214* (2013.01); *A61B 17/1215* (2013.01); *A61B 17/1219* (2013.01); *A61B 17/12022* (2013.01); *A61B 17/12031* (2013.01); *A61B 17/12145* (2013.01); *A61B 17/12168* (2013.01); *A61B 17/12172* (2013.01); *A61F 2/04* (2013.01); *A61B 2017/00867* (2013.01); *A61F 2002/043* (2013.01)

(56) References Cited

U.S. PATENT DOCUMENTS

| | | |
|---|---|---|
| 4,153,058 A | 5/1979 | Nehme |
| 4,233,984 A | 11/1980 | Walling |
| 4,245,624 A | 1/1981 | Komiya |
| 4,479,792 A | 10/1984 | Lazarus et al. |
| 4,494,531 A | 1/1985 | Gianturco |
| 4,532,935 A | 8/1985 | Wang |
| 4,702,260 A | 10/1987 | Wang |
| 4,739,760 A | 4/1988 | Chin et al. |
| 4,766,906 A | 8/1988 | Wang |
| 4,769,017 A | 9/1988 | Fath et al. |
| 4,821,722 A | 4/1989 | Miller et al. |
| 4,880,015 A | 11/1989 | Nierman |
| 5,056,529 A | 10/1991 | de Groot |
| 5,084,012 A | 1/1992 | Kelman |
| 5,108,368 A | 4/1992 | Hammerslag et al. |
| 5,165,420 A | 11/1992 | Strickland |
| 5,186,167 A | 2/1993 | Kolobow |
| 5,190,546 A | 3/1993 | Jervis |
| 5,219,895 A | 6/1993 | Kelman |
| 5,240,011 A | 8/1993 | Assa |
| 5,261,889 A | 11/1993 | Laine et al. |
| 5,303,714 A | 4/1994 | Abele et al. |
| 5,312,329 A | 5/1994 | Beaty et al. |
| 5,312,331 A | 5/1994 | Knoepfler |
| 5,315,992 A | 5/1994 | Dalton |
| 5,334,183 A | 8/1994 | Wuchinich |
| 5,342,387 A | 8/1994 | Summers |
| 5,354,287 A | 10/1994 | Wacks |
| 5,385,606 A | 1/1995 | Kowanko |
| 5,423,830 A | 6/1995 | Schneebaum et al. |
| 5,472,017 A | 12/1995 | Kovalcheck |
| 5,479,938 A | 1/1996 | Weier |
| 5,484,401 A | 1/1996 | Rodriguez et al. |
| 5,514,536 A | 5/1996 | Taylor |
| 5,522,819 A | 6/1996 | Graves et al. |
| 5,526,821 A | 6/1996 | Jamshidi |
| 5,549,551 A | 8/1996 | Peacock, III et al. |
| 5,549,904 A | 8/1996 | Juergensen et al. |
| 5,599,294 A | 2/1997 | Edwards et al. |
| 5,660,175 A | 8/1997 | Dayal |
| 5,660,185 A | 8/1997 | Shmulewitz et al. |
| 5,697,365 A | 12/1997 | Pel |
| 5,735,264 A | 4/1998 | Siczek et al. |
| 5,736,132 A | 4/1998 | Juergensen et al. |
| 5,750,657 A | 5/1998 | Edwardson et al. |
| 5,762,070 A | 6/1998 | Nagamatsu |
| 5,846,235 A | 12/1998 | Pasricha et al. |
| 5,875,692 A | 3/1999 | Lin |
| 5,895,417 A | 4/1999 | Pomeranz et al. |
| 5,916,210 A | 6/1999 | Winston |
| 5,916,212 A | 6/1999 | Baust et al. |
| 5,938,635 A | 8/1999 | Kuhle |
| 5,954,636 A | 9/1999 | Schwartz et al. |
| 5,957,919 A | 9/1999 | Laufer |
| 5,964,770 A | 10/1999 | Flomenblit et al. |
| 5,972,026 A | 10/1999 | Laufer et al. |
| 5,978,697 A | 11/1999 | Maytal et al. |
| 6,063,111 A | 5/2000 | Hieshima et al. |
| 6,066,090 A | 5/2000 | Yoon |
| 6,080,113 A | 6/2000 | Heneveld et al. |
| 6,083,255 A | 7/2000 | Laufer et al. |
| 6,123,665 A | 9/2000 | Kawano |
| 6,174,323 B1 | 1/2001 | Biggs et al. |
| 6,183,498 B1 | 2/2001 | DeVore et al. |
| 6,196,966 B1 | 3/2001 | Kerin et al. |
| 6,200,333 B1 | 3/2001 | Laufer |
| 6,245,090 B1 | 6/2001 | Gilson et al. |
| 6,258,100 B1 | 7/2001 | Alferness et al. |
| 6,267,732 B1 | 7/2001 | Heneveld et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,287,304 B1 | 9/2001 | Eggers et al. |
| 6,293,951 B1 | 9/2001 | Alferness et al. |
| 6,299,633 B1 | 10/2001 | Laufer |
| 6,306,141 B1 | 10/2001 | Jervis |
| 6,310,166 B1 | 10/2001 | Hickey et al. |
| 6,312,428 B1 | 11/2001 | Eggers et al. |
| 6,315,737 B1 | 11/2001 | Skinner |
| 6,328,689 B1 | 12/2001 | Gonzalez et al. |
| 6,328,701 B1 | 12/2001 | Terwilliger |
| 6,352,503 B1 | 3/2002 | Matsui et al. |
| 6,379,373 B1 | 4/2002 | Sawhney et al. |
| 6,387,044 B1 | 5/2002 | Tachibana et al. |
| 6,390,967 B1 | 5/2002 | Forman et al. |
| 6,398,775 B1 | 6/2002 | Perkins et al. |
| 6,402,701 B1 | 6/2002 | Kaplan et al. |
| 6,402,754 B1 | 6/2002 | Gonzalez |
| 6,402,781 B1 | 6/2002 | Langberg et al. |
| 6,411,852 B1 | 6/2002 | Danek et al. |
| 6,416,554 B1 | 7/2002 | Alferness et al. |
| 6,443,944 B1 | 9/2002 | Doshi et al. |
| 6,447,534 B2 | 9/2002 | Cragg et al. |
| 6,464,648 B1 | 10/2002 | Nakamura |
| 6,474,340 B1 | 11/2002 | Vaska et al. |
| 6,478,730 B1 | 11/2002 | Bala et al. |
| 6,485,407 B2 | 11/2002 | Alferness et al. |
| 6,485,436 B1 | 11/2002 | Truckai et al. |
| 6,488,673 B1 | 12/2002 | Laufer et al. |
| 6,491,706 B1 | 12/2002 | Alferness et al. |
| 6,494,844 B1 | 12/2002 | Van Bladel et al. |
| 6,494,897 B2 | 12/2002 | Sterman et al. |
| 6,509,031 B1 | 1/2003 | Miller et al. |
| 6,514,290 B1 | 2/2003 | Loomas |
| 6,514,522 B2 | 2/2003 | Domb |
| 6,527,761 B1 | 3/2003 | Soltesz et al. |
| 6,537,195 B2 | 3/2003 | Forman |
| 6,537,314 B2 | 3/2003 | Langberg et al. |
| 6,540,694 B1 | 4/2003 | Van Bladel et al. |
| 6,540,716 B1 | 4/2003 | Holm |
| 6,549,800 B1 | 4/2003 | Atalar et al. |
| 6,551,255 B2 | 4/2003 | Van Bladel et al. |
| 6,551,302 B1 | 4/2003 | Rosinko et al. |
| 6,552,172 B2 | 4/2003 | Marx et al. |
| 6,558,337 B2 | 5/2003 | Dvorak et al. |
| 6,568,387 B2 | 5/2003 | Davenport et al. |
| 6,569,166 B2 | 5/2003 | Gonzalez |
| 6,577,893 B1 | 6/2003 | Besson et al. |
| 6,585,639 B1 | 7/2003 | Kotmel et al. |
| 6,589,161 B2 | 7/2003 | Corcoran |
| 6,592,559 B1 | 7/2003 | Pakter et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,622,731 B2 | 9/2003 | Daniel et al. |
| 6,629,951 B2 | 10/2003 | Laufer et al. |
| 6,632,222 B1 | 10/2003 | Edwards et al. |
| 6,632,239 B2 | 10/2003 | Snyder et al. |
| 6,632,243 B2 | 10/2003 | Zadno-Azizi et al. |
| 6,634,363 B1 | 10/2003 | Danek et al. |
| 6,638,275 B1 | 10/2003 | McGaffigan et al. |
| 6,645,205 B2 | 11/2003 | Ginn |
| 6,652,516 B1 | 11/2003 | Gough |
| 6,652,520 B2 | 11/2003 | Moorman et al. |
| 6,653,525 B2 | 11/2003 | Ingenito et al. |
| 6,663,624 B2 | 12/2003 | Edwards et al. |

(56) References Cited

U.S. PATENT DOCUMENTS

| | | |
|---|---|---|
| 6,679,264 B1 | 1/2004 | Deem et al. |
| 6,682,520 B2 | 1/2004 | Ingenito |
| 6,685,626 B2 | 2/2004 | Wironen |
| 6,689,072 B2 | 2/2004 | Kaplan et al. |
| 6,690,976 B2 | 2/2004 | Fenn et al. |
| 6,692,494 B1 | 2/2004 | Cooper et al. |
| 6,694,977 B1 | 2/2004 | Federowicz et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,709,408 B2 | 3/2004 | Fisher |
| 6,709,456 B2 | 3/2004 | Langberg et al. |
| 6,712,812 B2 | 3/2004 | Roschak et al. |
| 6,716,180 B2 | 4/2004 | Fontenot |
| 6,723,095 B2 | 4/2004 | Hammerslag |
| 6,730,044 B2 | 5/2004 | Stephens et al. |
| 6,736,822 B2 | 5/2004 | McClellan et al. |
| 6,749,606 B2 | 6/2004 | Keast et al. |
| 6,752,767 B2 | 6/2004 | Turovskiy et al. |
| 6,752,812 B1 | 6/2004 | Truwit |
| 6,758,824 B1 | 7/2004 | Miller et al. |
| 6,768,425 B2 | 7/2004 | Flaherty et al. |
| 6,770,066 B1 | 8/2004 | Weaver et al. |
| 6,770,070 B1 | 8/2004 | Balbierz |
| 6,789,545 B2 | 9/2004 | Littrup et al. |
| 6,790,172 B2 | 9/2004 | Alferness et al. |
| 6,790,185 B1 | 9/2004 | Fisher et al. |
| 6,797,001 B2 | 9/2004 | Mathis et al. |
| 6,807,446 B2 | 10/2004 | Fenn et al. |
| 6,808,525 B2 | 10/2004 | Latterell et al. |
| 6,814,778 B1 | 11/2004 | Farnworth |
| 6,817,973 B2 | 11/2004 | Merril et al. |
| 6,825,091 B2 | 11/2004 | Bae et al. |
| 6,827,086 B2 | 12/2004 | Shuman |
| 6,827,683 B2 | 12/2004 | Otawara |
| 6,830,756 B2 | 12/2004 | Hnojewyj |
| 6,840,243 B2 | 1/2005 | Deem et al. |
| 6,840,948 B2 | 1/2005 | Albrecht et al. |
| 6,840,952 B2 | 1/2005 | Saker et al. |
| 6,843,767 B2 | 1/2005 | Corcoran et al. |
| 6,849,262 B2 | 2/2005 | Ollerenshaw et al. |
| 6,852,108 B2 | 2/2005 | Barry et al. |
| 6,860,847 B2 | 3/2005 | Alferness et al. |
| 6,863,676 B2 | 3/2005 | Lee et al. |
| 6,875,209 B2 | 4/2005 | Zvuloni et al. |
| 6,878,106 B1 | 4/2005 | Herrmann |
| 6,878,141 B1 | 4/2005 | Perkins et al. |
| 6,886,558 B2 | 5/2005 | Tanaka |
| 6,901,927 B2 | 6/2005 | Deem et al. |
| 6,902,526 B2 | 6/2005 | Katzman |
| 6,902,536 B2 | 6/2005 | Manna et al. |
| 6,904,909 B2 | 6/2005 | Andreas et al. |
| 6,907,881 B2 | 6/2005 | Suki et al. |
| 6,908,440 B2 | 6/2005 | Fisher |
| 6,918,881 B2 | 7/2005 | Miller et al. |
| 6,929,637 B2 | 8/2005 | Gonzalez et al. |
| 6,936,014 B2 | 8/2005 | Vetter et al. |
| 6,941,950 B2 | 9/2005 | Wilson et al. |
| 6,942,627 B2 | 9/2005 | Huitema |
| 6,945,942 B2 | 9/2005 | Van Bladel et al. |
| 6,962,587 B2 | 11/2005 | Johnson et al. |
| 6,964,662 B2 | 11/2005 | Kidooka |
| 6,967,673 B2 | 11/2005 | Ozawa et al. |
| 6,979,344 B2 | 12/2005 | Jones et al. |
| 6,986,737 B2 | 1/2006 | Suzuki et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,063,682 B1 | 6/2006 | Whayne et al. |
| 7,100,616 B2 | 9/2006 | Springmeyer |
| 7,112,225 B2 | 9/2006 | Ginn |
| 7,128,747 B2 | 10/2006 | Ginn |
| 7,141,046 B2 | 11/2006 | Perkins et al. |
| 7,165,548 B2 | 1/2007 | Deem et al. |
| 7,175,619 B2 | 2/2007 | Koblish et al. |
| 7,195,017 B2 | 3/2007 | Tanaka |
| 7,198,635 B2 | 4/2007 | Danek et al. |
| 7,300,428 B2 | 11/2007 | Ingenito |
| 7,351,202 B2 | 4/2008 | Long |
| 7,393,330 B2 | 7/2008 | Keast et al. |
| 7,393,363 B2 | 7/2008 | Ginn |
| 7,445,010 B2 | 11/2008 | Kugler et al. |
| 7,451,765 B2 | 11/2008 | Adler |
| 7,503,931 B2 | 3/2009 | Kowalsky et al. |
| 7,517,320 B2 | 4/2009 | Wibowo et al. |
| 7,549,984 B2 | 6/2009 | Mathis |
| 7,608,579 B2 | 10/2009 | Gong et al. |
| 7,662,181 B2 | 2/2010 | Deem et al. |
| 7,670,282 B2 | 3/2010 | Mathis |
| 7,731,651 B2 | 6/2010 | Pearce et al. |
| 7,757,691 B2 | 7/2010 | Reynolds et al. |
| 7,766,891 B2 | 8/2010 | McGurk et al. |
| 7,766,895 B2 | 8/2010 | Soltesz et al. |
| 7,766,938 B2 | 8/2010 | McGurk et al. |
| 7,775,968 B2 | 8/2010 | Mathis |
| 7,896,008 B2 | 3/2011 | Tanaka |
| 8,142,455 B2 | 3/2012 | Thompson et al. |
| 8,157,823 B2 | 4/2012 | Aronson et al. |
| 8,157,837 B2 | 4/2012 | Thompson et al. |
| 8,282,660 B2 | 10/2012 | Thompson et al. |
| 8,632,605 B2 | 1/2014 | Thompson et al. |
| 8,668,707 B2 | 3/2014 | Thompson et al. |
| 8,721,734 B2 | 5/2014 | Mathis et al. |
| 8,740,921 B2 | 6/2014 | Mathis et al. |
| 8,888,800 B2 | 11/2014 | Mathis et al. |
| 8,932,310 B2 | 1/2015 | Thompson et al. |
| 2001/0051799 A1 | 12/2001 | Ingenito |
| 2002/0007831 A1 | 1/2002 | Davenport et al. |
| 2002/0026188 A1 | 2/2002 | Balbierz et al. |
| 2002/0042564 A1 | 4/2002 | Cooper et al. |
| 2002/0042565 A1 | 4/2002 | Cooper et al. |
| 2002/0062120 A1 | 5/2002 | Perkins et al. |
| 2002/0077593 A1 | 6/2002 | Perkins et al. |
| 2002/0091379 A1 | 7/2002 | Danek et al. |
| 2002/0111620 A1 | 8/2002 | Cooper et al. |
| 2002/0112729 A1 | 8/2002 | DeVore et al. |
| 2002/0128647 A1 | 9/2002 | Roschak et al. |
| 2002/0138074 A1 | 9/2002 | Keast et al. |
| 2002/0161392 A1* | 10/2002 | Dubrul ................ A61F 2/958 606/200 |
| 2002/0161399 A1 | 10/2002 | Cruise et al. |
| 2002/0176893 A1 | 11/2002 | Wironen et al. |
| 2002/0183244 A1 | 12/2002 | Ollerenshaw et al. |
| 2002/0183838 A1 | 12/2002 | Liddicoat et al. |
| 2002/0188171 A1 | 12/2002 | Alferness et al. |
| 2003/0018318 A1 | 1/2003 | Melsky |
| 2003/0029452 A1 | 2/2003 | Suki et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0069488 A1 | 4/2003 | Alferness et al. |
| 2003/0070676 A1 | 4/2003 | Cooper et al. |
| 2003/0070682 A1 | 4/2003 | Wilson et al. |
| 2003/0070683 A1 | 4/2003 | Deem et al. |
| 2003/0075170 A1 | 4/2003 | Deem et al. |
| 2003/0083671 A1 | 5/2003 | Rimbaugh et al. |
| 2003/0083692 A1 | 5/2003 | Vbra et al. |
| 2003/0088195 A1 | 5/2003 | Vardi et al. |
| 2003/0100921 A1 | 5/2003 | Addis et al. |
| 2003/0109866 A1 | 6/2003 | Edwards et al. |
| 2003/0127090 A1 | 7/2003 | Gifford et al. |
| 2003/0130657 A1 | 7/2003 | Tom et al. |
| 2003/0154988 A1 | 8/2003 | DeVore et al. |
| 2003/0158515 A1 | 8/2003 | Gonzalez et al. |
| 2003/0159700 A1 | 8/2003 | Laufer et al. |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0191496 A1 | 10/2003 | Edwards et al. |
| 2003/0192551 A1 | 10/2003 | Deem et al. |
| 2003/0195385 A1 | 10/2003 | DeVore |

(56) References Cited

U.S. PATENT DOCUMENTS

| | | |
|---|---|---|
| 2003/0195511 A1 | 10/2003 | Barry |
| 2003/0212337 A1 | 11/2003 | Sirokman |
| 2003/0212412 A1 | 11/2003 | Dillard et al. |
| 2003/0212450 A1 | 11/2003 | Schlick |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0024356 A1 | 2/2004 | Tanaka |
| 2004/0030262 A1 | 2/2004 | Fisher et al. |
| 2004/0031494 A1 | 2/2004 | Danek et al. |
| 2004/0034357 A1 | 2/2004 | Beane et al. |
| 2004/0038868 A1 | 2/2004 | Ingenito |
| 2004/0040555 A1 | 3/2004 | Tanaka |
| 2004/0049187 A1 | 3/2004 | Burnett et al. |
| 2004/0049264 A1 | 3/2004 | Sowinski et al. |
| 2004/0052850 A1 | 3/2004 | Schankereli |
| 2004/0055606 A1 | 3/2004 | Hendricksen et al. |
| 2004/0059263 A1 | 3/2004 | De Vore et al. |
| 2004/0063613 A1 | 4/2004 | Rolke et al. |
| 2004/0072756 A1 | 4/2004 | Wilkie et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073207 A1 | 4/2004 | Ginn |
| 2004/0073241 A1 | 4/2004 | Barry et al. |
| 2004/0078054 A1 | 4/2004 | Biggs et al. |
| 2004/0081676 A1 | 4/2004 | Schankereli et al. |
| 2004/0087886 A1 | 5/2004 | Gellman |
| 2004/0120849 A1 | 6/2004 | Stewart et al. |
| 2004/0133168 A1 | 7/2004 | Salcudean et al. |
| 2004/0134487 A1 | 7/2004 | Deem et al. |
| 2004/0154621 A1 | 8/2004 | Deem et al. |
| 2004/0158228 A1 | 8/2004 | Perkins |
| 2004/0172058 A1 | 9/2004 | Edwards et al. |
| 2004/0176801 A1 | 9/2004 | Edwards et al. |
| 2004/0176833 A1 | 9/2004 | Pavenik et al. |
| 2004/0210248 A1 | 10/2004 | Gordon et al. |
| 2004/0211434 A1 | 10/2004 | Loomas et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0234575 A1 | 11/2004 | Horres et al. |
| 2004/0237966 A1 | 12/2004 | Tanaka |
| 2004/0244802 A1 | 12/2004 | Tanaka |
| 2004/0244803 A1 | 12/2004 | Tanaka |
| 2004/0267277 A1* | 12/2004 | Zannis .................. A61F 2/4618 606/99 |
| 2005/0004599 A1 | 1/2005 | McNally-Heintzelman et al. |
| 2005/0015106 A1 | 1/2005 | Perkins et al. |
| 2005/0016530 A1 | 1/2005 | McCutcheon et al. |
| 2005/0033310 A1 | 2/2005 | Alferness et al. |
| 2005/0033344 A1 | 2/2005 | Dillard et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0051163 A1 | 3/2005 | Deem et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0085801 A1 | 4/2005 | Cooper et al. |
| 2005/0096529 A1 | 5/2005 | Cooper et al. |
| 2005/0101836 A1 | 5/2005 | Onuki et al. |
| 2005/0103340 A1 | 5/2005 | Wondka |
| 2005/0107783 A1 | 5/2005 | Tom et al. |
| 2005/0119614 A1 | 6/2005 | Melsky |
| 2005/0131339 A1 | 6/2005 | Makin et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0148902 A1 | 7/2005 | Minar et al. |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178389 A1 | 8/2005 | Shaw et al. |
| 2005/0192526 A1 | 9/2005 | Biggs et al. |
| 2005/0196344 A1 | 9/2005 | McCutcheon et al. |
| 2005/0240277 A1 | 10/2005 | Aliski et al. |
| 2005/0244401 A1 | 11/2005 | Ingenito |
| 2005/0281739 A1 | 12/2005 | Gong et al. |
| 2005/0281740 A1 | 12/2005 | Gong et al. |
| 2005/0281796 A1 | 12/2005 | Gong et al. |
| 2005/0281797 A1 | 12/2005 | Gong et al. |
| 2005/0281798 A1 | 12/2005 | Gong et al. |
| 2005/0281799 A1 | 12/2005 | Gong et al. |
| 2005/0281800 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004305 A1 | 1/2006 | George et al. |
| 2006/0004388 A1 | 1/2006 | Whayne et al. |
| 2006/0004400 A1 | 1/2006 | McGurk et al. |
| 2006/0009748 A1 | 1/2006 | Mathis |
| 2006/0009801 A1 | 1/2006 | McGurk et al. |
| 2006/0020243 A1 | 1/2006 | Speck et al. |
| 2006/0025815 A1 | 2/2006 | McGurk et al. |
| 2006/0029548 A1 | 2/2006 | Pelleg et al. |
| 2006/0030863 A1 | 2/2006 | Fields et al. |
| 2006/0032497 A1 | 2/2006 | Doshi |
| 2006/0076023 A1 | 4/2006 | Rapacki et al. |
| 2006/0095002 A1 | 5/2006 | Soltesz et al. |
| 2006/0100666 A1 | 5/2006 | Wilkinson et al. |
| 2006/0116749 A1 | 6/2006 | Willink et al. |
| 2006/0118126 A1 | 6/2006 | Tanaka |
| 2006/0124126 A1 | 6/2006 | Tanaka |
| 2006/0135947 A1 | 6/2006 | Soltesz et al. |
| 2006/0135984 A1 | 6/2006 | Kramer et al. |
| 2006/0162731 A1 | 7/2006 | Wondka et al. |
| 2006/0167416 A1 | 7/2006 | Mathis et al. |
| 2006/0184016 A1 | 8/2006 | Glossop |
| 2006/0200076 A1 | 9/2006 | Gonzalez et al. |
| 2006/0206147 A1 | 9/2006 | DeVore et al. |
| 2006/0235432 A1 | 10/2006 | DeVore et al. |
| 2006/0235467 A1 | 10/2006 | DeVore et al. |
| 2006/0249164 A1 | 11/2006 | Springmeyer |
| 2006/0264772 A1 | 11/2006 | Aljuri et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2006/0283462 A1 | 12/2006 | Fields et al. |
| 2006/0287701 A1 | 12/2006 | Pal et al. |
| 2007/0005083 A1 | 1/2007 | Sabanathan et al. |
| 2007/0096048 A1 | 5/2007 | Clerc |
| 2007/0185572 A1 | 8/2007 | Solem et al. |
| 2007/0221230 A1 | 9/2007 | Thompson et al. |
| 2008/0036763 A1 | 2/2008 | Chen et al. |
| 2008/0063693 A1* | 3/2008 | Cook ...................... A61L 29/16 424/443 |
| 2008/0161865 A1* | 7/2008 | Hagen ..................... A61N 1/05 607/2 |
| 2008/0183204 A1* | 7/2008 | Greenhalgh ....... A61B 17/8858 606/198 |
| 2008/0200797 A1 | 8/2008 | Kotmel et al. |
| 2008/0262473 A1 | 10/2008 | Kornblau et al. |
| 2009/0012626 A1 | 1/2009 | Thompson et al. |
| 2009/0076526 A1 | 3/2009 | Rousseau et al. |
| 2009/0076622 A1 | 3/2009 | Thompson et al. |
| 2009/0076623 A1* | 3/2009 | Mathis ............. A61B 17/12022 623/23.65 |
| 2009/0104183 A1 | 4/2009 | Gong et al. |
| 2009/0221967 A1 | 9/2009 | Thommen et al. |
| 2009/0306644 A1 | 12/2009 | Mayse et al. |
| 2010/0070050 A1 | 3/2010 | Mathis et al. |
| 2010/0100196 A1 | 4/2010 | Thompson et al. |
| 2010/0297218 A1* | 11/2010 | Gong .................... A61L 24/043 424/450 |
| 2012/0123514 A1 | 5/2012 | Kunis |

(56) References Cited

U.S. PATENT DOCUMENTS

| | | | |
|---|---|---|---|
| 2012/0172909 A1 | 7/2012 | Mathis et al. |
| 2013/0096603 A1 | 4/2013 | Mathis et al. |
| 2013/0102887 A1 | 4/2013 | Thompson et al. |
| 2013/0103059 A1 | 4/2013 | Mathis et al. |
| 2013/0217956 A1 | 8/2013 | Thompson et al. |
| 2014/0188246 A1 | 7/2014 | Aronson et al. |
| 2014/0371705 A1 | 12/2014 | Mathis |
| 2015/0051709 A1 | 2/2015 | Vasquez et al. |
| 2015/0057695 A1 | 2/2015 | Mathis et al. |

FOREIGN PATENT DOCUMENTS

| | | |
|---|---|---|
| FR | 2840796 | 12/2003 |
| GB | 2324729 A | 1/2002 |
| JP | H04-22908 | 2/1992 |
| JP | 06209962 | 8/1994 |
| JP | 07010762 | 1/1995 |
| JP | 08322944 | 12/1996 |
| JP | H101998-5343 | 1/1998 |
| JP | 2001-505109 | 4/2001 |
| JP | 2001-505109 A | 4/2001 |
| JP | 2004-516067 A | 6/2004 |
| JP | 2005-503881 A | 2/2005 |
| JP | 2005-514106 A | 5/2005 |
| JP | 2005-287568 | 10/2005 |
| JP | 2006504441 | 2/2006 |
| JP | 2007-513721 A | 5/2007 |
| JP | 2009-502428 A | 1/2009 |
| JP | 2009-529966 A | 8/2009 |
| WO | WO 94/01508 A1 | 1/1994 |
| WO | WO 98/01084 A1 | 1/1998 |
| WO | WO 98/23227 | 6/1998 |
| WO | WO 00/13592 A1 | 3/2000 |
| WO | WO 01/13839 A1 | 3/2001 |
| WO | WO 01/54618 A1 | 8/2001 |
| WO | WO 02/00270 A1 | 1/2002 |
| WO | WO 02/00275 A1 | 1/2002 |
| WO | WO 02/02158 A1 | 1/2002 |
| WO | WO 02/49554 A1 | 6/2002 |
| WO | WO 03/05709 A1 | 1/2003 |
| WO | 03/022221 A1 | 3/2003 |
| WO | 03022807 | 3/2003 |
| WO | WO 03/028522 A2 | 4/2003 |
| WO | WO 03/077768 A1 | 9/2003 |
| WO | WO 2004/049970 A2 | 6/2004 |
| WO | WO 2004/062505 A1 | 7/2004 |
| WO | WO 2004/080347 A2 | 9/2004 |
| WO | WO 2004/086977 A1 | 10/2004 |
| WO | WO 2004/080347 A3 | 6/2005 |
| WO | WO 2005/058206 A1 | 6/2005 |
| WO | WO 2005/122870 A2 | 12/2005 |
| WO | WO 2007/016409 A1 | 2/2007 |
| WO | 2007035798 | 3/2007 |
| WO | WO 2007/106495 A2 | 9/2007 |
| WO | WO 2008/036763 A2 | 3/2008 |
| WO | WO 2014/151557 A2 | 9/2014 |

OTHER PUBLICATIONS

U.S. Appl. No. 14/453,372, filed Aug. 6, 2014 by Thompson et al. (Unpublished.).

English Translation and Office Action for corresponding Japanese Patent Application No. 2012-511968 dated Aug. 26, 2014, 6 pages.
Wikipedia, "Medical Ventilator", downloaded from Internet http://en/wikipedia.org/w/index.php?title+Medical_vntilator&printalbe=yes on Jan. 16, 2015, 5 pages.
U.S. Appl. No. 14/134,977, filed Dec. 19, 2013 by Aronson et al. (Unpublished.).
U.S. Appl. No. 14/162,124, filed Jan. 23, 2014 by Thompson et al. (Unpublished.).
Hermanson, Greg T. Bioconjugate Techniques. San Diego: Academic Press, Inc. 1996. (Table of contents only).
Lam, et al. X-Ray Diagnosis: A Physician's Approach. Singapore: Springer. 1998. (Table of contents only).
Rowe, et al. Handbook of Pharmaceutical Excipients. 4th Edition. London: Pharmaceutical Press. 2003. (Table of contents only).
Slone, et al. Body CT: A Practical Approach. New York: McGraw-Hill. 2000. (Table of contents only).
Stout, et al. X-Ray Structure Determination: A Practical Guide. 2nd Edition. New York: John Wiley & Sons. 1989. (Table of contents only).
The United States Pharmacopeia. 29th Revision. 2006. The United States Pharmacopeia Convention. Rockville, MD. (Table of contents only).
U.S. Appl. No. 60/885,305, filed Jan. 17, 2007; first named inventor: David Thompson.
Supplementary European Search Report of EP Application No. 07752999.8, mailed Sep. 22, 2009, 12 pages total.
International Search Report and Written Opinion of PCT Application No. PCT/US2009/056839, mailed on Jan. 4, 2010, 15 pages total.
International Search Report of PCT Application No. PCT/US07/06339, dated May 14, 2008, 5 pages total.
International Search Report and Written Opinion of PCT Application No. PCT/US2010/035297, mailed Jul. 20, 2010, 14 pages total.
US Office Action of U.S. Appl. No. 12/782,515 to Mathis et al. mailed Jun. 29, 2012, 11 pages.
US Final Office Action of U.S. Appl. No. 12/782,515 to Mathis et al. mailed Feb. 15, 2013, 10 pages.
US Office Action of U.S. Appl. No. 12/782,515 to Mathis et al. mailed Aug. 2, 2013. 10 pages.
US Notice of Allowance of U.S. Appl. No. 12/782,515 to Mathis et al. mailed Dec. 27, 2013, 9 pages.
International Written Opinion of PCT Application No. PCT/US07/06339, dated May 21, 2008, 12 pages total.
O'Brien et al. "Improvements in Lung Function, Exercise, and Quality of Life in Hypercapnic COPD Patients After Lung Volume Reduction Surgery". Chest 115 (1999): 75-84.
Quint et al. "Diaphragmetic Shape Change After Lung Volume Reduction Surgery". Journal of Thoracic Imaging 16 (2001):149-155.
Yusen et al. "A Prospective Evaluation of Lung Volume Reduction Surgery in 200 Consecutive Patients." Chest 123 (2003):1026-1037.
Office Action for Japanese Patent Application No. 2009-500440, May 11, 2012, 3 pages.
English Translation of Office Action for corresponding Japanese Application No. 2012-511968 mailed on Nov. 21, 2013, 5 pages.
English Translation of Office Action for corresponding Chinese Application No. 201080030290.4 mailed on Jan. 26, 2014, 11 pages.
Extended European Search Report for corresponding European Patent Application No. 14188364.5 dated May 29, 2015, 12 pages.

* cited by examiner

FIG. 5A
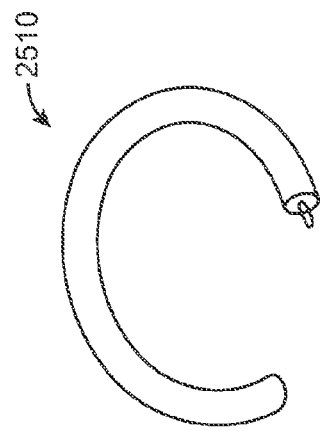
FIG. 5B
FIG. 5C
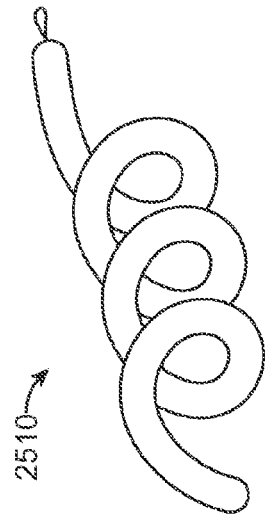
FIG. 5D

CROSS-SECTIONAL MODIFICATION DURING DEPLOYMENT OF AN ELONGATE LUNG VOLUME REDUCTION DEVICE

CROSS-REFERENCES TO RELATED APPLICATIONS

The present application is a Divisional of U.S. Ser. No. 12/782,515 filed May 18, 2010 (Allowed), which application claims the benefit under 35 USC 119(e) of U.S. Provisional Application No. 61/179,306 filed May 18, 2009. The full disclosures of which are incorporated herein by reference in their entirety for all purposes.

This application is generally related to U.S. application Ser. No. 12/167,167 filed on Jul. 2, 2008 (now U.S. Pat. No. 8,282,660), entitled Minimally Invasive Lung Volume Reduction Devices, Methods, and Systems, which is a continuation application of PCT Appln. No. PCT/US07/06339 filed on Mar. 13, 2007, which is a continuation-in-part of U.S. patent application Ser. No. 11/422,047 filed Jun. 2, 2006 (now U.S. Pat. No. 8,157,837), entitled Minimally Invasive Lung Volume Reduction Device and Method, each of which are incorporated herein by reference in their entirety for all purposes.

This application is also generally related to U.S. Provisional Patent Applns. 60/743,471 filed Mar. 13, 2006; entitled Minimally Invasive Lung Volume Reduction Device and Method; 60/884,804 filed Jan. 12, 2007, entitled Minimally Invasive Lung Volume Reduction Devices, Methods and Systems; and 60/885,305 filed Jan. 17, 2007, entitled Minimally Invasive Lung Volume Reduction Devices, Methods and Systems, each of which are incorporated herein by reference in their entirety for all purposes.

This application is also generally related to co-assigned and concurrently filed U.S. patent application Ser. No. 12/209,631, entitled Delivery of Minimally Invasive Lung Volume Reduction Devices (now U.S. Pat. No. 8,142,455); Ser. No. 12/209,662 entitled Improved Lung Volume Reduction Devices, Methods and Systems (now U.S. Pat. No. 8,157,823), both of which were filed Sep. 12, 2008; and to Ser. No. 12/558,206, entitled Enhanced Efficacy Lung Volume Reduction Devices, Methods, and Systems; and Ser. No. 12/558,197, entitled Elongated Lung Volume Reduction Devices, Methods, and Systems (now U.S. Pat. No. 8,632,605), each of which were filed Sep. 11, 2009, all of which are incorporated herein by reference in their entirety for all purposes.

All publications and patent applications mentioned in this specification are herein incorporated by reference to the same extent as if each individual publication or patent application was specifically and individually indicated to be incorporated by reference.

BACKGROUND OF THE INVENTION

Field of the Invention

Devices, systems and methods are described for treating lungs. The devices, systems and methods improve the quality of life and restore lung function for patients suffering from emphysema. The systems consist of an implant and a delivery catheter that can be advanced through tortuous anatomy and actuated to retain a pre-determined shape and rigidity. The actuated implant modifies the shape of the airways and locally compresses lung parenchyma to cause volume reduction and thereby tensions the lung parenchyma to restore elastic recoil. Systems and devices are also included that deploy and actuate the implantable devices, as well as systems and devices designed for recapture of the implanted device.

Current medical literature describes emphysema as a chronic (long-term) lung disease that can get worse over time. It's usually caused by smoking. Having emphysema means some of the air sacs in your lungs are damaged, making it hard to breathe. Some reports indicate that emphysema is the fourth largest cause of mortality in the U.S., affecting an estimated 16-30 million U.S. citizens. Each year approximately 100,000 sufferers die of the disease. Smoking has been identified as a major cause, but with ever increasing air pollution and other environmental factors that negatively affect pulmonary patients; the number of people affected by emphysema is on the rise.

A currently available solution for patients suffering from emphysema is a surgical procedure called Lung Volume Reduction (LVR) surgery whereby diseased lung is resected and the volume of the lung is reduced. This allows healthier lung tissue to expand into the volume previously occupied by the diseased tissue and allows the diaphragm to recover. High mortality and morbidity may be associated with this invasive procedure. Several minimally invasive investigational therapies exist that aim at improving the quality of life and restoring lung function for patients suffering from emphysema. These potential therapies include mechanical devices and biological treatments. The Zephyr™ device by Emphasys (Redwood City Calif.) and the IBV™ device by Spiration (Redmond Wash.) are mechanical one way valve devices. The underlying theory behind these devices is to achieve absorptive atelectasis by preventing air from entering diseased portion of the lung, while allowing air and mucous to pass through the device out of the diseased regions. The Watanabe spigot is another mechanical device that can seek to completely occlude the airway, thereby preventing air from entering and exiting the lung. Collateral ventilation (interlobar and intralobar—porous flow paths that prevent complete occlusion) may prevents atelectasis for such devices. The lack of atelectasis or lung volume reduction can drastically reduces the effectiveness of such devices. Other mechanical devices include means of deploying anchors into airways and physically deforming airways by drawing the anchors together via cables.

Biological treatments utilize tissue engineering aimed at causing scarring at specific locations. Unfortunately, it can be difficult to control the scarring and to prevent uncontrolled proliferation of scarring.

BRIEF SUMMARY OF THE INVENTION

The present invention generally provides improved medical devices, systems, and methods, particularly for treating one or both lungs of a patient. Embodiments of the invention often make use of elongate implant structures which can be introduced into an airway system to a target airway axial region. The target axial region may or may not include branches, and the implants can be deployed within the airway by allowing the implant to bend so that the implant compresses adjacent lung tissue. Many embodiments may apply lateral bending and/or compression forces against the lung tissue from within the airways for an extended period of time. Exemplary embodiments include structures or features which may inhibit tissue reactions that might otherwise allow portions of the device to eventually traverse through the wall of the airway. Many embodiments of the elongate devices may enhance the support area bearing laterally on the tissue of a surrounding airway lumen wall, particularly along a length of the device between a proximal end of the device and a distal end of the device. Embodiments may have features which increase the device friction with the airway to allow the device to grip the surrounding airway as the device is deployed. This may help prevent the device from longitudinally sliding within the airway and may increase gathering of the damaged lung tissue together in compression. Maintaining the device within the airway may facilitate recapture of the device (either in the delivery catheter or after full deployment and the device has been implanted, optionally using a separate device to capture the implant with a separate grasper) and successfully pull the device out of the lung. By infusing an appropriate adhesive around the device in the lung, ideally by infusing a Pneu-Seal™ albumin-glutaraldehyde adhesive, the device may be recaptured by pulling the device out of the sealant. To minimize or inhibit inflammation to the tissue, the device should comprise materials that are biocompatible and generally rounded such that micro motion between the device and airway don't cause an acceleration of tissue degradation. Contact with the device may advantageously induce beneficial tissue thickening. Features which induce some tissue ingrowth (stimulation of tissue growth) so the tissue foundation is thickened and the device is better supported can also be beneficial.

In a first aspect, the invention provides a method for treating a lung of a patient. The lung including an airway system having a plurality of branching airways, and the method comprises advancing an implant distally into the airway system while the implant is in a delivery configuration. The implant has an elongate length defining an axis with a lateral profile having a lateral bearing surface transverse to the axis. The implant is deployed within the airway such that the implant expands laterally from the axis of the implant so as to increase the lateral bearing surface. Lung tissue is locally compressed along the implant by bearing laterally against a luminal surface of the airways with the expanded bearing surface of the implant so that the expansion inhibits penetration of the implant through the airway, and so that tension in other lung tissue of the patient is increased sufficiently to enhance lung function.

Advantageously, enhancing tension in a portion of the lung (and particularly in a relatively healthy portion of the lung) can increase the overall lung function despite significant collateral flow between branches of the airway system. The local compression of a selected portion of the lung tissue may enhance tension in other lung tissue because the overall volume occupied by the lung is constrained by the surrounding tissue structures. In many embodiments, deploying the implant within the implant system comprises bending the implant within the airways so that the implant bends a first axial airway region toward a second axial airway region so as to locally compress the portion of lung tissues between the first and second axial airway regions. The first and second axial airway regions will typically surround a first portion of the implant and a second portion of the implant, the implant portions typically being offset along the axis of the implant. In most embodiments, lateral expansion of the implant includes resilient lateral expansion, the implant typically being laterally constrained within a lumen of a delivery catheter during advancing of the implant into the airway system. Similarly, the compressing of the lung tissue can be effected by resilient bending of the implant toward a relaxed configuration, the delivery catheter often constraining the axis of the implant toward a sufficiently straight configuration to facilitate advancing the implant into the airway system.

In some embodiments, the implant may comprise a laterally bent or rolled sheet (or thin plate) material when the implant is in the delivery configuration. The lateral expanding of the implant may then comprise laterally flattening or unrolling of the sheet material. The flattened or unrolled sheet material will typically have first and second opposed major surfaces and the bearing surface may include at least a portion of the first major surface, for example. Alternative laterally expandable structures may also be used. For example, the lateral expanding of the implant may comprise radial expansion of a radially expandable structure. In such embodiments, the implant may also include a shaft or wire extending axially along the radially expandable structure, with the radially expandable structure defining the bearing surface and being urged laterally by the shaft so as to effect compression of the lung tissue. Radial expansion may be effected by increasing lateral separation of struts defined between cuts or slots along a tube analogous to the expansion of any of a wide variety of stent structures, with the tube defining the radially expandable body. The radial expansion of the implant body may comprises radial expansion of a braided sleeve, the braided sleeve defining the radially expandable body and shortening axially during radial expansion. The lateral expansion of the implant may, in some embodiments, comprise bending of at least one wire or filament from an axial configuration (the wire typically extending along a shaft of the implant in the delivery configuration). The at least one wire or filament may define the bearing surface and may be urged laterally by the shaft so as to effect compression of the lung tissue.

In another aspect, the invention provides a method for treating a lung of a patient. The lung including an airway system having a plurality of branching airways, and the method comprises advancing an implant distally into the airway system while the implant is in a delivery configuration. The implant has a proximal end, a distal end, and an elongate length defining an axis therebetween. The implant can have a lateral bearing surface transverse to the axis, and can be deployed within the airway system by axially bending the implant so that the lateral bearing surface of the implant bends a first axial airway region toward a second axial airway region and locally compresses lung tissues between the first and second axial airway regions. An interface between the bearing surface of the deployed implant and the airway may be hydrophilic and/or locally enhanced along the axis of the implant during deployment so as to inhibit damage to the airway during long-term implantation such that tension in other lung tissue of the patient remains sufficient to enhance lung function.

In some embodiments, deploying the implant within the implant system will comprise introducing adhesive around the implant so that the adhesive inhibits penetration of the implant through an airway wall. The adhesive may be advanced within a lumen of the delivery catheter that also surrounds the implant, through a smaller adhesive delivery catheter that can be advanced through the lumen of the delivery catheter, through an annular space between the delivery catheter and a surrounding sheath, through a second lumen of the delivery catheter, or the like. Optionally, the implant may comprise an axial series of plugs or lateral protrusions, with the implant bending at least in-part between the plugs or protrusions. The plugs or protrusions can locally inhibit penetration of the implant through an airway wall without constricting axial bending. Other embodiments may, when deployed in the airway system, orient a major surface of a thin, wide elongate body so as to engage and bear against the luminal surface, with the orientation varying along the length of the implant so as to promote compression of three-dimensional lung tissue volumes by corresponding curvature in three dimensions. In some exemplary embodiments, the bearing surface of the implant comprises a polymer material. Surprisingly, the polymer material may be sufficiently hydrophilic for biofilm formation inhibition when the implant is disposed in the lung. For example, the implant may comprise a resilient metal shaft disposed within a sleeve of the polymer material, the sleeve comprising a polycarbonate-polyurethane copolymer.

In another aspect, the invention provides an implant for treating a lung of a patient, the lung including an airway system having a plurality of branching airways, the implant comprises an elongate body having a proximal end and a distal end defining an axis therebetween. The elongate body has a delivery configuration and a deployed configuration, the elongate body in the delivery configuration having a lateral profile and a lateral bearing surface transverse to the axis. The axis of the elongate body in the delivery configuration is sufficiently straight for advancement distally into the airway system. The elongate body is deployable from the delivery configuration to the deployed configuration within the airway system such that the implant expands laterally from the axis of the implant to increase the lateral bearing surface. Deployment of the elongate body within the airway may also effect bending of the elongate body within the airway system so that the bearing surface bears laterally against a luminal surface of the airways. Engagement by the bearing surface against the surrounding airway can be sufficient to bend the airway while the expanded bearing surface of the implant inhibits penetration of the implant through the airway. The bending of the airway induces local compression of lung tissue so as to enhance tension in other lung tissue of the patient sufficiently to enhance lung function of the patient.

In another aspect, the invention provides an implant for treating a lung of a patient, the lung including an airway system having a plurality of branching airways, the implant comprising an implant body having a proximal end, a distal end, and an elongate length defining an axis therebetween. The implant body has a lateral bearing surface transverse to the axis, the implant body also having a delivery configuration in which the axis of the implant body is sufficiently straight for axial advancement distally into the airway system. The implant body is deployable from the delivery configuration to a deployed configuration within the airway system by axially bending the implant sufficiently that the lateral bearing surface of the implant bends a first axial airway region toward a second axial airway region so as to compresses lung tissues between the first and second axial airway regions. An interface between the bearing surface of the deployed implant and the airway is hydrophilic and/or locally expanded along the axis of the implant so as to inhibit damage to the airway during long-term implantation.

BRIEF DESCRIPTION OF THE DRAWINGS

A better understanding of the features and advantages of the present invention will be obtained by reference to the attached documents that set forth illustrative embodiments, in which the principles of the invention are utilized, and the accompanying drawings of which:

FIGS. 5A-5D illustrates devices in a variety of deployed conditions;

DETAILED DESCRIPTION OF THE INVENTION

Figure 1A:
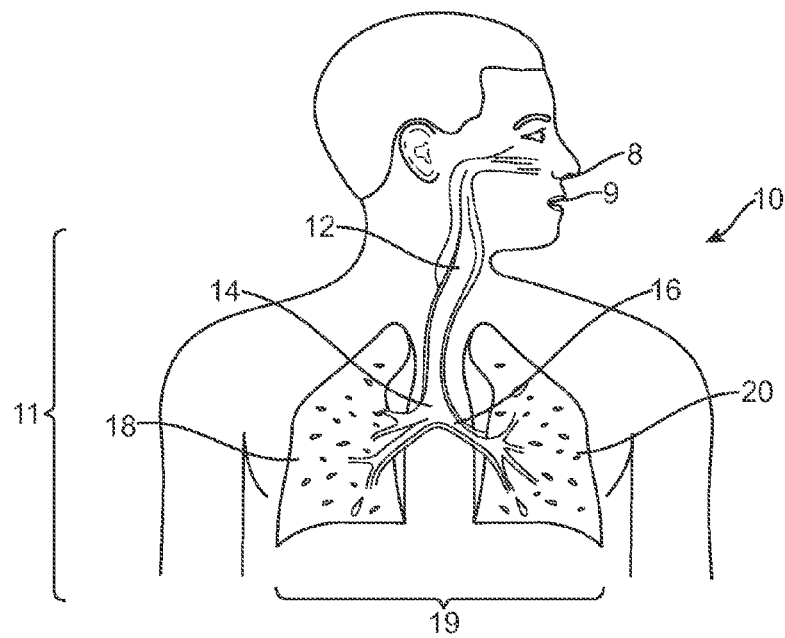
FIGS. 1A-C illustrates the anatomy of the respiratory system.

By way of background and to provide context for the invention, FIG. 1A illustrates the respiratory system 10 located primarily within a thoracic cavity 11. This description of anatomy and physiology is provided in order to facilitate an understanding of the invention. Persons of skill in the art, will appreciate that the scope and nature of the invention is not limited by the anatomy discussion provided. Further, it will be appreciated there can be variations in anatomical characteristics of an individual, as a result of a variety of factors, which are not described herein. The respiratory system 10 includes the trachea 12, which brings air from the nose 8 or mouth 9 into the right primary bronchus 14 and the left primary bronchus 16. From the right primary bronchus 14 the air enters the right lung 18; from the left primary bronchus 16 the air enters the left lung 20. The right lung 18 and the left lung 20, together comprise the lungs 19. The left lung 20 is comprised of only two lobes while the right lung 18 is comprised of three lobes, in part to provide space for the heart typically located in the left side of the thoracic cavity 11, also referred to as the chest cavity.

Figure 1B:
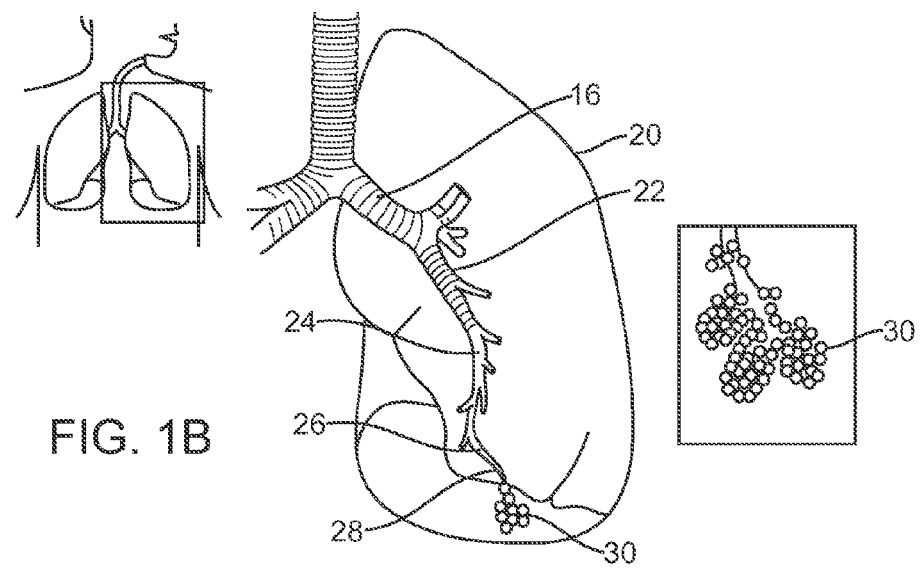
Figure 1C:
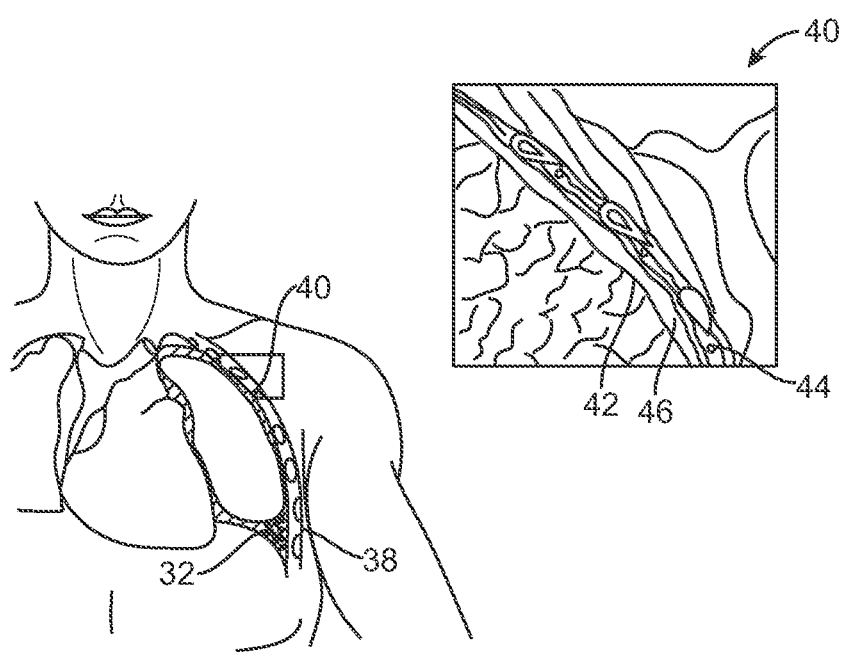
Figure 2A:
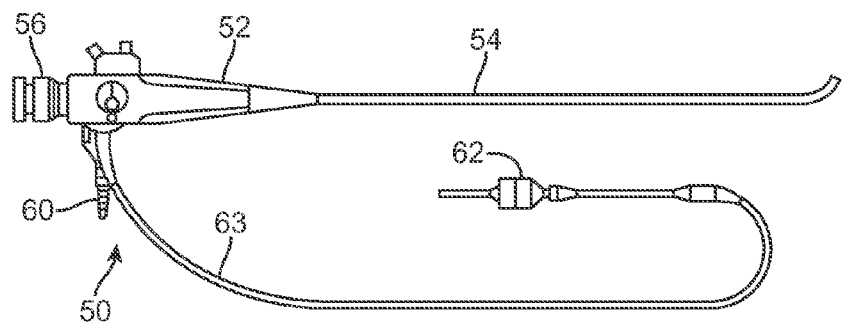
FIGS. 2A-D illustrate a bronchoscope.
Figure 2B:
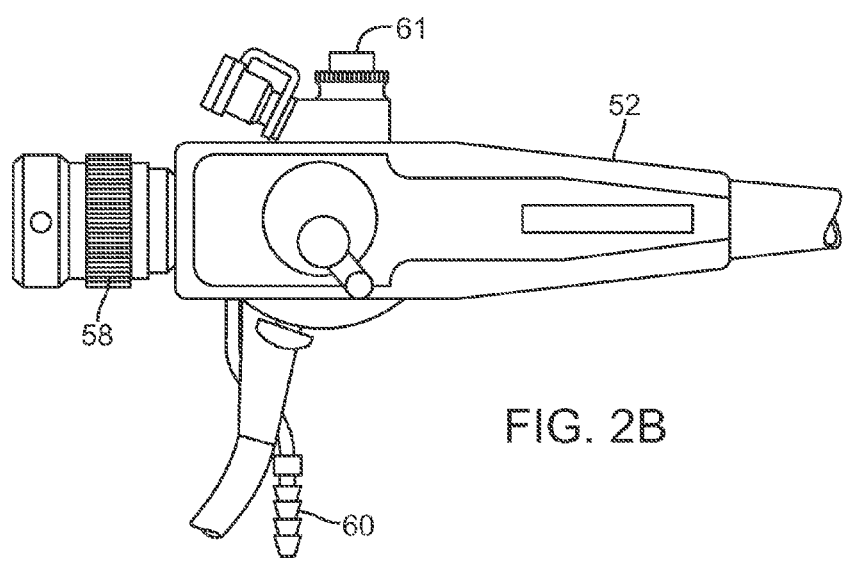
Figure 2C:
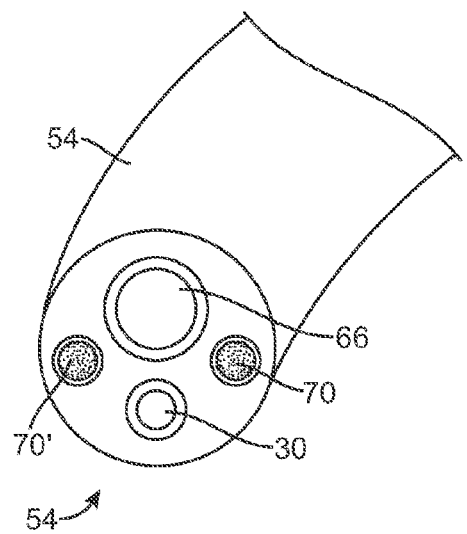
Figure 2D:
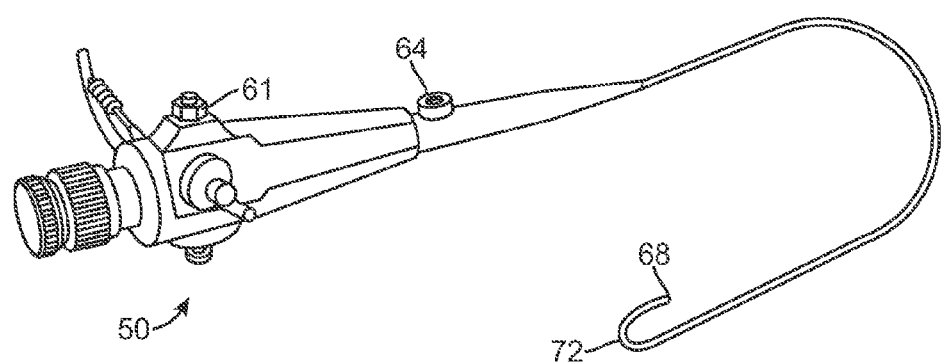

As shown in more detail in FIG. 1B, the primary bronchus, e.g. left primary bronchus 16, that leads into the lung, e.g. left lung 20, branches into secondary bronchus 22, and then further into tertiary bronchus 24, and still further into bronchioles 26, the terminal bronchiole 28 and finally the alveoli 30. The pleural cavity 38 is the space between the lungs and the chest wall. The pleural cavity 38 protects the lungs 19 and allows the lungs to move during breathing. As shown in FIG. 1C, the pleura.40 defines the pleural cavity 38 and consists of two layers, the visceral pleurae 42 and the parietal pleurae 44, with a thin layer of pleural fluid therebetween. The space occupied by the pleural fluid is referred to as the pleural space 46. Each of the two pleurae layers 42, 44, are comprised of very porous mesenchymal serous membranes through which small amounts of interstitial fluid transude continually into the pleural space 46. The total amount of fluid in the pleural space 46 is typically slight. Under normal conditions, excess fluid is typically pumped out of the pleural space 46 by the lymphatic vessels.

The lungs 19 are described in current literature an elastic structure that float within the thoracic cavity 11. The thin layer of pleural fluid that surrounds the lungs 19 lubricates the movement of the lungs within the thoracic cavity 11.

Suction of excess fluid from the pleural space 46 into the lymphatic channels maintains a slight suction between the visceral pleural surface of the lung pleura 42 and the parietal pleural surface of the thoracic cavity 44. This slight suction creates a negative pressure that keeps the lungs 19 inflated and floating within the thoracic cavity 11. Without the negative pressure, the lungs 19 collapse like a balloon and expel air through the trachea 12. Thus, the natural process of breathing out is almost entirely passive because of the elastic recoil of the lungs 19 and chest cage structures. As a result of this physiological arrangement, when the pleura 42, 44 is breached, the negative pressure that keeps the lungs 19 in a suspended condition disappears and the lungs 19 collapse from the elastic recoil effect.

When fully expanded, the lungs 19 completely fill the pleural cavity 38 and the parietal pleurae 44 and visceral pleurae 42 come into contact. During the process of expansion and contraction with the inhaling and exhaling of air, the lungs 19 slide back and forth within the pleural cavity 38. The movement within the pleural cavity 38 is facilitated by the thin layer of mucoid fluid that lies in the pleural space 46 between the parietal pleurae 44 and visceral pleurae 42. As discussed above, when the air sacs in the lungs are damaged 32, such as is the case with emphysema, it is hard to breathe. Thus, isolating the damaged air sacs to improve the elastic structure of the lung improves breathing. Similarly, locally compressing diseased regions of the lung tissue while maintaining an overall volume of the lung increases tension in other portions of the lung tissue, which can increase the overall lung function.

A conventional flexible bronchoscope is described in U.S. Pat. No. 4,880,015 to Nierman for Biopsy Forceps. As shown in FIGS. 2A-D, bronchoscope 50 can be configured to be of any suitable length, for example, measuring 790 mm in length. The bronchoscope 50 can further be configured from two main parts, a working head 52 and an insertion tube 54. The working head 52 contains an eyepiece 56; an ocular lens with a diopter adjusting ring 58; attachments for the suction tubing 60 and a suction valve 61 and for the cold halogen light source 62 and 63; and an access port or biopsy inlet 64, through which various devices and fluids can be passed into the working channel 66 and out the distal end of the bronchoscope. The working head is attached to the insertion tube, which typically measures 580 mm in length and 6.3 mm in diameter. The insertion tube can be configured to contain fiberoptic bundles (which terminate in the objective lens 30 at the distal tip 68), two light guides 70, 70' and the working channel 66. The distal end of the bronchoscope has the ability to bend 72 anterior and posterior only, with the exact angle of deflection depending on the instrument used. A common range of bending is from 160 degrees forward to 90 degrees backward, for a total of 250 degrees. Bending is controlled by the operator by adjusting an angle lock lever 74 and angulation lever 76 on the working head. See also, U.S. Patent Pub. US 2005/0288550 A1 to Mathis for Lung Access Device and US 2005/0288549 A1 to Mathis for Guided Access to Lung Tissue.

Figure 3:
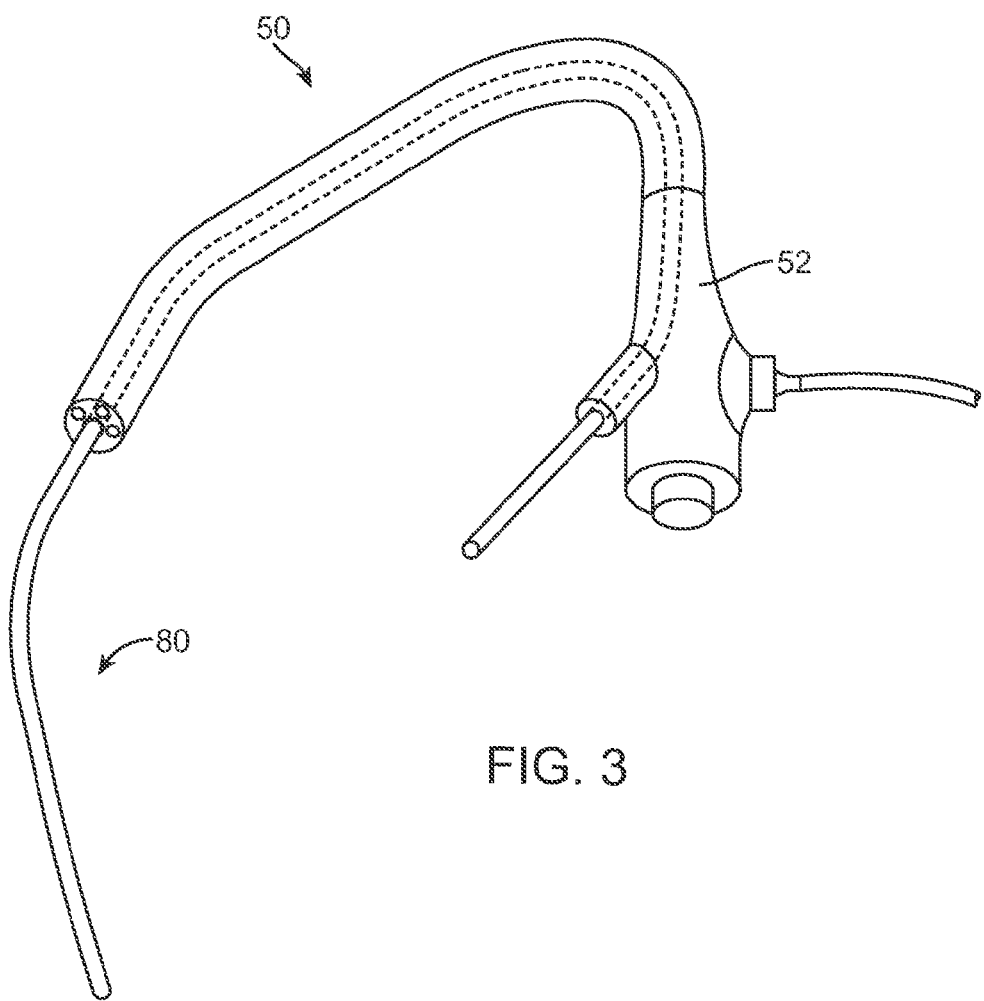
FIG. 3 illustrates a bronchoscope in combination with a delivery device for a lung volume reduction device according to the invention.

FIG. 3 illustrates the use of a lung volume reduction delivery device 80 for delivering a lung volume reduction device comprising an implantable device with the bronchoscope SO. The lung volume reduction system, as described in further detail below, is adapted and configured to be delivered to a lung airway of a patient in a delivered configuration and then changed to a deployed configuration. By deploying the device, tension can be applied to the surrounding tissue which can facilitate restoration of the elastic recoil of the lung. The device is designed to be used by an interventionalist or surgeon.

Figure 4A:
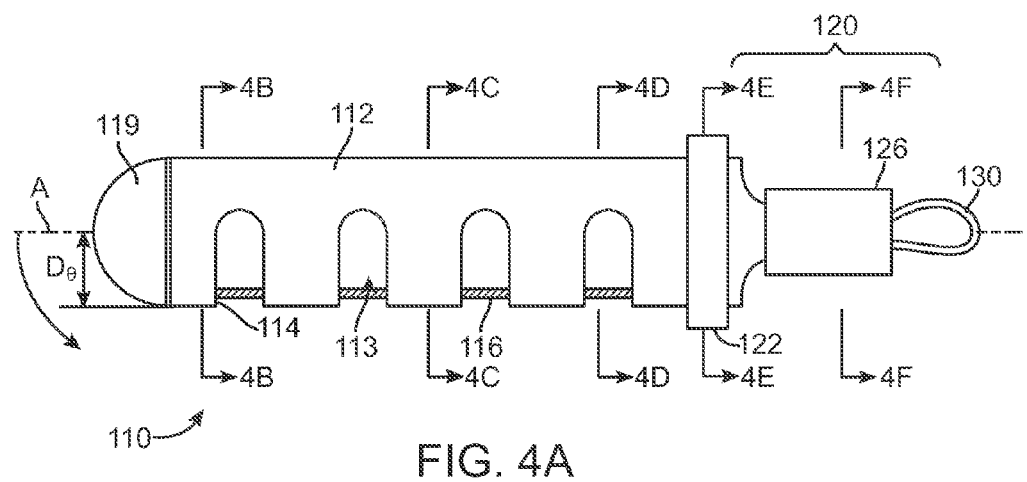
FIGS. 4A-4F illustrate a lung volume reduction device according to an aspect of the invention.
Figure 4B:
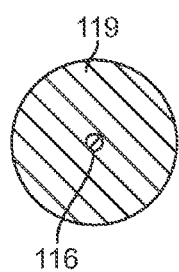
Figure 4C:
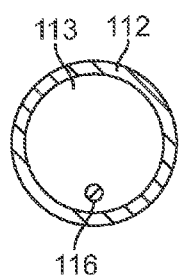
Figure 4D:
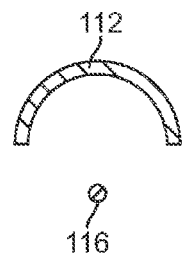
Figure 4E:
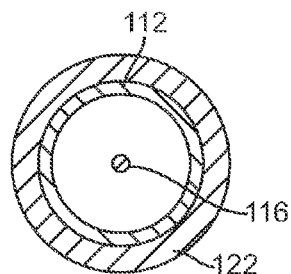
Figure 4F:
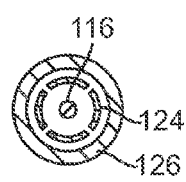

FIGS. 4A-F illustrate a shaft or tubular member of a lung volume reduction device 110 which may be included in an implant according to an aspect of the invention, with FIGS. 4B-F being cross-sections taken along the lines B-B, C-C, D-D, E-E and F-F of FIG. 4A, respectively. As will be described in more detail below, the complete implant may include additional structures or materials which enhance the ability of the implant to provide therapeutic benefits during long-term implantation, with many of these additional structures or materials providing a bearing surface or interface between the compression-inducing shaft of the device and the surrounding tissue lumen wall of an airway. The function and properties of these additional structures and materials may be understood after first reviewing the shaft or other compression-inducing portion of the implant in isolation. Toward that end, the lung volume reduction device 110 includes a member, such as tubular member 112, which has c-cuts 114, or notches, along its length to provide flexibility such that the device can be deflected off a longitudinal axis A when deployed. In other words, the longitudinal axis of the implant shaft or body may be changed from a generally straight configuration suitable for distal insertion along axis A to a bent or deployed configuration, the implant ideally bending a surrounding airway in the bent configuration so as to locally compress lung tissue. For example, where the cuts are oriented parallel each other along the length of the tubular member and are of the same or similar depth D, the device will tend to uniformly curve around an axis point when deployed (depicted below). As a result, the device preferentially curls or bends in a direction as determined by the shape of the slots. Different types (width, depth, orientation, etc.) of notches or slots can be used to achieve different operational effects and configurations of the deployed device without departing from the scope of the invention.

Positioned within a lumen 113 of the tubular member 112 is an actuation element 116 or pull-wire. The actuation element can have a circular circumference in cross-section, as depicted, or can have any other suitable cross-section. The actuation element 116 is anchored at one end of the device 110, e.g. the distal end, by a cap 119. The cap 119 can be bonded to the catheter and a distal crimp can be provided to crimp the cap into the pull wire. The rounded cap can also be provided to make the tip of the device atraumatic. The opposing end, e.g. proximal end, is adapted and configured to engage a mechanism 120. The mechanism enables the device to be deployed. The mechanism can further be adapted and configured to enable the device to lock into a deployed configuration once the device 110 is deployed or unlocked to retrieve the device. The device 110 is configured to be detachable from a delivery catheter adapted to deliver the lung volume reduction device (discussed below).

Mechanism 120, at the proximal end of the device, can be adapted to include a retainer ring 122 that engages a ratchet 124 that can be used to lock the device in place. The coupler 126 retains the ratchet 124 such that the ratchet locks the device in place once deployed. At the proximal end a retrieval adapter 130 is provided, such as a pull-wire eyelid. The retrieval adapter 130 is adapted and configured to enable the device to be retrieved at a later point during the procedure or during a subsequent procedure. The ratchet device has flanges that extend away from a central axis when deployed to lock the device in place.

FIGS. 5B-D illustrates implant devices 2510 according to the invention in a variety of deployed configurations. FIG. 5A illustrates the device 2510 having a longitudinal configuration, such as the configuration assumed prior to deployment. When the device is implanted and placed in compression or tension axially, the device will preferentially bend. The actual preferential bending will vary depending upon the configuration of the device. For example, the location, depth, and orientation of the slots depicted in FIGS. 4-8; or the orientation of the walls of the segments of FIG. 9. As FIG. 5B illustrates, for example, where the device 2510 has evenly spaced c-cuts or notches along its length the device will preferentially bend such that the walls of forming the "c" or notch will approach each other, or pinch together, resulting in a deployed device that has preferentially bent into a curved "c" shape (see, FIGS. 4-5). This results because as tension is applied on the actuation device, or wire, the implant deforms and the wire takes a shorter path. FIG. 5C illustrates a device deployed into an "S" shape, such as would be achieved using a configuration like that depicted in FIG. 6. As will be appreciated, the S-shape could continue, much like a sine wave, in an many curves as desired depending upon the configuration of the device. FIG. 5D illustrates a device deployed into a spiral configuration. As will be appreciated by those skilled in the art upon reviewing this disclosure, other configurations can be achieved by, for example, altering the size and location of the c-cuts on the tubular member, or by altering the configuration of segments. Once the device preferentially bends, the device imparts a bending force on the lung tissue which results in a reduction of lung volume. As is appreciated, from the configurations shown in FIG. 5 the implant, once re-shaped, is shorter in length than the deliverable implant configuration. The shortening occurs when for example, the distance between the proximal end and the distal end is reduced. Typically, the deliverable shape of the device is such that it fits within a cylindrical space that is 18 mm in diameter or smaller. Thus, the implant can come into contact with tissue that is larger than $10^{-6}$ square inches per linear inch of the implant length. The re-shaped or deployed implant can be configured in a variety of shapes to lie within a single plane, or to adopt any other suitable configuration, such that it does not lie within a single plane. Additionally, the device can have varying rates of curvature along its length.

Figure 6A:
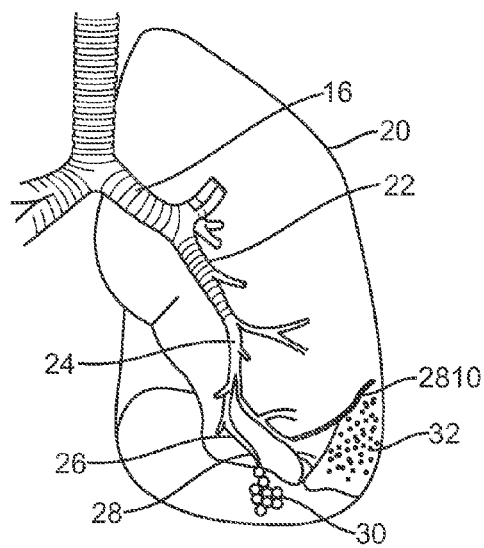
FIGS. 6A-C illustrate a device implanted within the lungs.
Figure 6B:
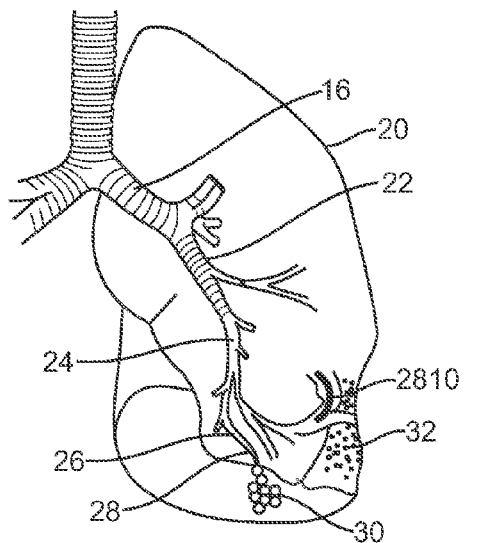
Figure 6C:
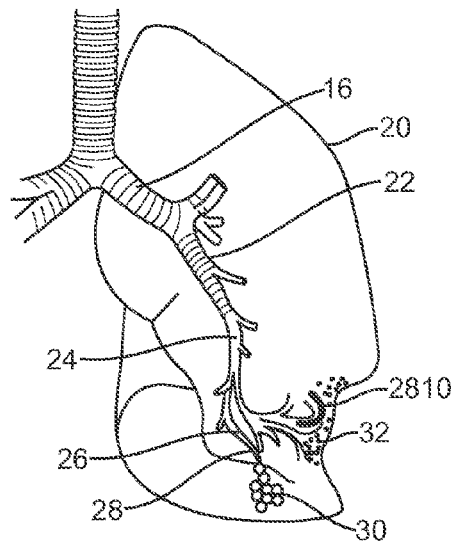

FIGS. 6A-C illustrates the process of implanting the device within a lung. As is evidence, the device 2810 is advanced is a configuration where the device adapts to the anatomy of the lungs through the airways and into, for example, the bronchioles until it reaches a desired location relative to the damaged tissue 32. The device is then activated by engaging the actuation device, causing the device to curve and pull the lung tissue toward the activated device (see, FIG. 6B). The device continues to be activated until the lung tissue is withdrawn or compressed a desired amount, such as depicted in FIG. 6C. As will be appreciated by those skilled in the art, withdrawing or compressing the tissue can be achieved by, for example, curving and compressing a target section of lung tissue upon deployment of one of the configurable devices disclosed herein such that other portions of the lung are tensioned sufficiently to provide a desired improvement in lung function. Once activated sufficiently, the deployment device is withdrawn from the lung cavity.

Figure 7A:
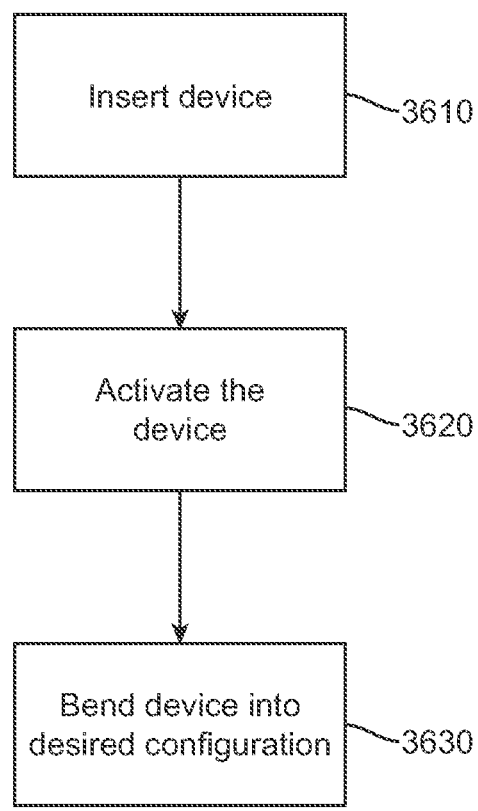
FIG. 7A illustrates a method steps for implanting the device.

A variety of steps for performing a method according to the invention would be appreciated by those skilled in the art upon review of this disclosure. However, for purposes of illustration, FIG. 7A illustrates the steps including, insertion of the device 3610, activating the device 3620, such as by activating an actuator; bending the device into a desired configuration 3630 and locking the device into a deployed condition. As will be appreciated the step of bending the device can be achieved by activating the actuator, as described above, or by the implant being restored into a preconfigured shape. In both cases, the bending of the device within an airway will preferably locally compress lung tissue so as to increase tissue tension in other portions of the lung. Exemplary embodiments may include laterally expanding the device from the axis of the implant shaft or body when the device is activated 3620 so as to inhibit perforation of the device through an airway wall. Still further options may include introducing adhesive or the like before, during, and/or after bending of the device 3630.

In one embodiment, the device operation includes the step of inserting a bronchoscope into a patient's lungs and then inserting an intra-bronchial device or lung volume reduction device into the bronchoscope. The intrabronchial device is then allowed to exit the distal end of the bronchoscope where it is pushed into the airway. A variety of methods can then be used to verify the positioning of the device to determine if the device is in the desired location. Suitable methods of verification include, for example, visualization via visualization equipment, such as fluoroscopy, CT scanning, etc. Thereafter the device is activated by pulling the pull wire proximally (i.e., toward the user and toward the exterior of the patient's body). At this point, another visual check can be made to determine whether the device has been positioned and deployed desirably. Thereafter, the device can be fully actuated and the ratchet can be allowed to lock and hold the device in place. Thereafter, the implant is decoupled from the delivery catheter and the delivery catheter is removed.

Figure 7B:
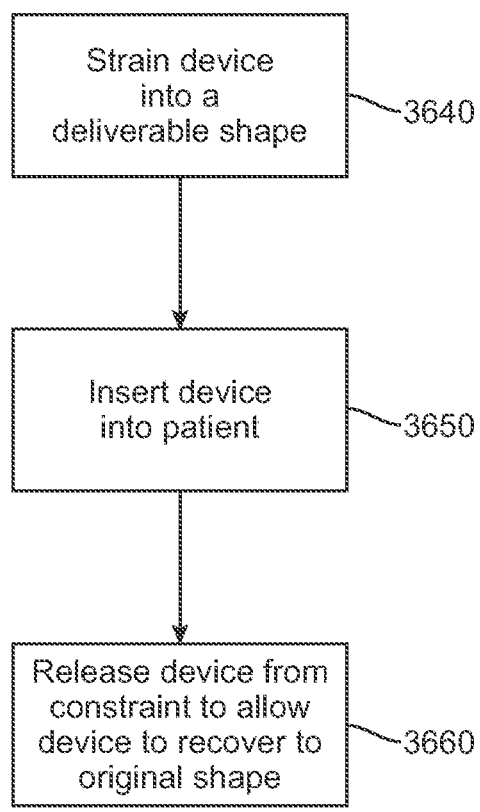
FIG. 7B illustrates a method steps for implanting the device.

Another method of tensioning the lung is shown in FIG. 7B which illustrates steps that include, applying bending loads or force to strain a device from a first shape into a deliverable shape without plastically or permanently bending the device 3640, delivering the device into the patient using the bronchoscope or other delivery system components to hold the device in a deliverable shape while it is being introduced 3650 and then removing the constraint used to hold the device to allow it to recover back to it's first shape 3660. Elastic recovery of the device will drive the device to a more bent condition that will apply force to nearby lung tissue. The bending forces locally compress tissue near the implant and apply tension on lung tissue in surrounding regions to restore lung recoil and enhance breathing efficiency. The first shape is adapted to be elastically constrained by a delivery device to a deliverable configuration whereby removal of the delivery device allows the implant to recoil and be reshaped closer to its first shape. Straining of the device into a deliverable shape 3640 may also include constraining the device laterally toward an axis of the device as described below. Release of the device 3660 may then allow the device to expand laterally from the deliverable configuration to a deployed configuration. As a result, the deployed device can present a larger lateral tissue-engaging surface per unit of axial length of the device than the lateral surface presented by the device in the deliverable configuration.

Figure 8:
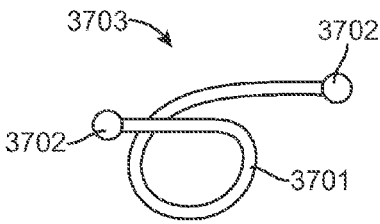
FIG. 8 illustrates a device configuration.

FIG. 8 shows an example of an implantable device 3703 comprising Nitinol metal wire 3701. Nickel-Titanium, Titanium, stainless steel or other biocompatible metals with memory shape properties or materials with capabilities to recover after being strained 1% or more may be used to make such an implant. Additionally, plastics, carbon based composites or a combination of these materials would be suitable. The device is shaped like a French horn and can generally lie in a single plane. The ends are formed into a shape that maximizes surface area shown in the form of balls 3702 to minimize scraping or gouging lung tissue. The balls may be made by melting back a portion of the wire, however, they may be additional components that are welded, pressed or glued onto the ends of wire 3701.

A Nitinol metallic implant, such as the one illustrated in FIG. 8, may be configured to be elastic to recover to a desired shape in the body as any other type of spring would or it can be made in a configuration that may be thermally actuated to recover to a desired shape. Nitinol can be cooled to a martensite phase or warmed to an austenite phase. In the austenite phase, the metal recovers to its programmed shape. The temperature at which the metal has fully converted to an austenite phase is known as the Af temperature (austenite final). If the metal is tuned so that the Af temperature is at body temperature or lower than body temperature, the material is considered to be elastic in the body and it will perform as a simple spring. The device can be cooled to induce a martensite phase in the metal that will make the device flexible and very easy to deliver. As the device is allowed to heat, typically due to body heat, the device will naturally recover its shape because the metal is making a transition back to an austenite phase. If the device is strained to fit through a delivery system, it may be strained enough to induce a martensite phase also. This transformation can take place with as little as 0.1% strain. A device that is strain induced into a martensite phase will still recover to its original shape and convert back to austenite after the constraints are removed. If the device is configured with an Ar temperature that is above body temperature, the device may be heated to convert it to austenite and thermally activate its shape recovery inside the body. All of these configurations will work well to actuate the device in the patient's lung tissue. The human body temperature is considered to be 37 degrees C. in the typical human body.

Figure 9:
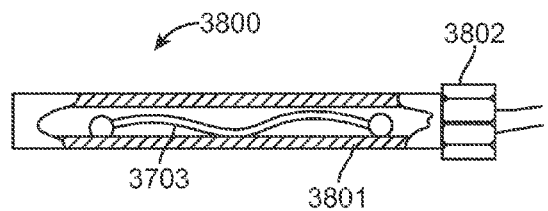
FIG. 9 illustrates a device in a loading cartridge.

FIG. 9 illustrates a cutaway view of a delivery cartridge system 3800 that constrains the implant device 3703 in a deliverable shape. The device 3801 may be shipped to the intended user in such a system or it may be used as a tool to more easily load the implant into a desired shape before being installed into the patient, bronchoscope or a catheter delivery device. The cartridge may be sealed or terminated with open ends or one or more hubs such as the Luer lock hub 3802 that is shown. The implant should be constrained to a diameter that is the same or less than 18 mm diameter because anything larger than that will be difficult to advance past the vocal cord opening.

Figure 10:
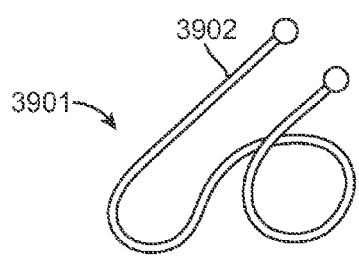
FIG. 10 illustrates a long device configuration.

FIG. 10 illustrates another implant device 3901 that is shaped in a three dimensional shape similar to the seam of a baseball. The wire is shaped so that proximal end 3902 extends somewhat straight and slightly longer than the other end. This proximal end will be the end closest to the user and the straight section will make recapture easier. If it were bent, it may be driven into the tissue making it hard to access.

Figure 11:
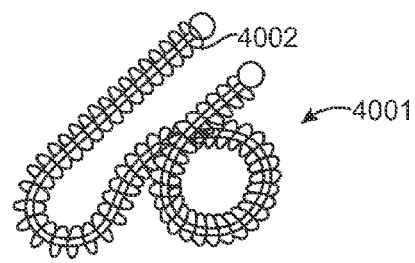
FIG. 11 illustrates a device configuration with a wire support frame.

FIG. 11 is an illustration of another implant system 4001. It is similar to that shown in FIG. 10 with the addition of a wire frame 4002 surrounding the device. The wire frame may be used, for example, to increase the bearing area that is applied to the lung tissue. By increasing the bearing area, the pressure born by the tissue is reduced along with a reduction in the propensity for the device to grow through lung structures or cause inflammatory issues. Small wires that apply loads in the body tend to migrate so we believe that the device should be configured to possess more than 0.000001 ($1^{-6}$ in$^2$) square inches of surface area per linear inch of the length of the device. The frame is one of many ways to provide a larger surface area to bear on the tissue. Alternative frames or structures may expand laterally from an axis of the device as the device is deployed.

Figure 12:
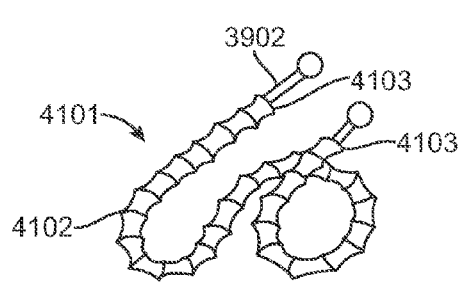
FIG. 12 illustrates a device configuration with a covering.

FIG. 12 shows yet another example of a device 4101 according to the invention. The device 4101 features a covering to increase bearing area 4102. In this example, the main wire 3902 is covered by a wire frame and a polymeric covering 4102. The covering may be made of any biocompatible plastic, thermoplastic, fluoropolymer, Teflon®, urethane, metal mesh, coating, silicone or other resilient material that will reduce the bearing pressure on the lung tissue. The ends of the covering 4103 may remain sealed or open as shown to allow the user to flush antibiotics into and out of the covering. In exemplary embodiments, the covering 4102 (and/or other implant/tissue interface structures, particularly non-metallic implant interface structures) may comprise a hydrophilic polymer, with the polymer preferably being sufficiently hydrophilic to inhibit formation of a biofilm. Suitable hydrophilic polymers may comprise polycarbonate urethanes (PCUs) such as those used for coating cardiac pacemaker leads and the like. Exemplary PCUs include relatively high durometer PCUs such as a 55D PCU, as is commercially available from a variety of sources. The covering may optionally comprise a sleeve of such a polymer, with the sleeve having an outer cross-section about the same as the rounded atraumatic surfaces of the balls or the like at the proximal and distal ends of the device. The sleeve may optionally be affixed to the device by an adhesive disposed in the annular space between the sleeve and the shaft or wire of the device between the ends. Similar materials may be used for other bearing-area enhancing structures described herein, and/or as coatings on such structures.

Figure 13:
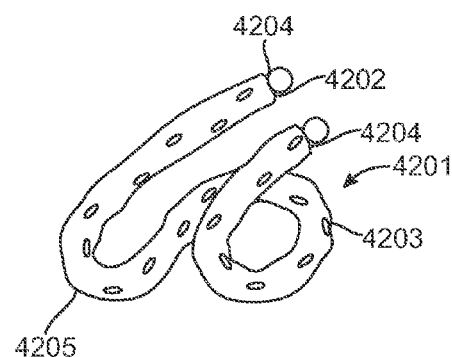
FIG. 13 illustrates a device configuration with a perforated covering.

FIG. 13 illustrates another configuration of the implant device 4201 showing a covering 4205 with perforations 4203 adapted and configured to allow the device to be flushed. The ends 4202 of the covering are sealed to the ends of the device to keep the two components fixed and prevent sliding of one or the other during deployment. The covering may be thermally bonded, glued or shrunk to a tight fit.

Figure 14:
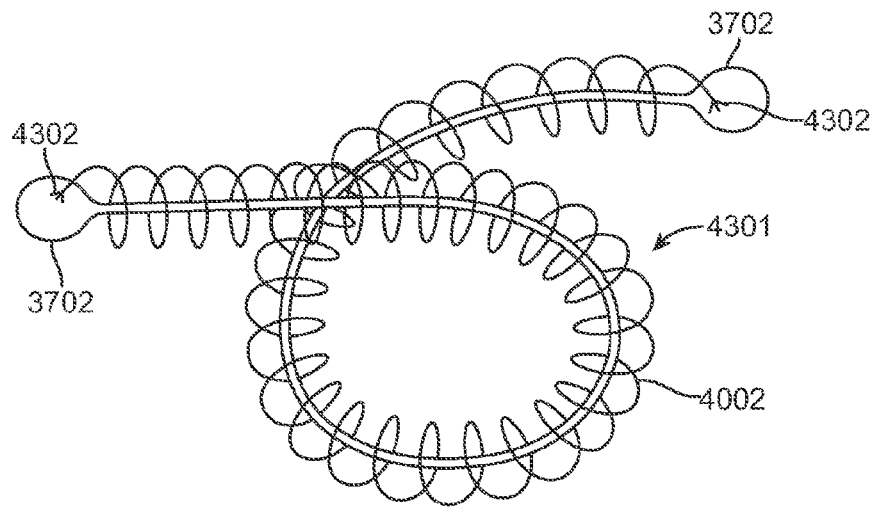
FIG. 14 illustrates a device configuration with an attached wire support frame.

FIG. 14 illustrates a device 4301 that has the wire frame 4002 joined to the ball ends 3702 at a junction 4302. The balls may be melted from the wire stock and the wire frame may be incorporated into the ball at that time. It may also be glued, pressed together, welded or mechanically locked together.

Figure 15:
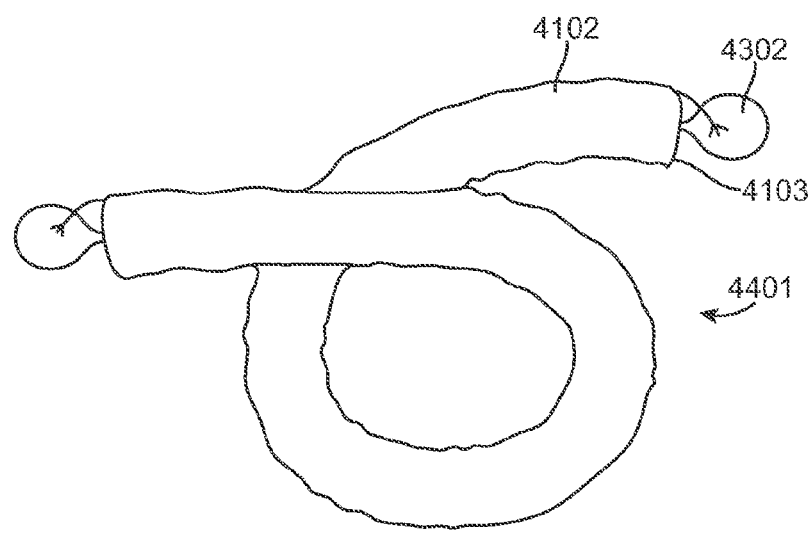
FIG. 15 illustrates a device configuration with an attached frame and covering.

FIG. 15 illustrates another implant device 4401 with an attached wire frame 4302, main wire 4103 and a covering 4102.

Figure 16:
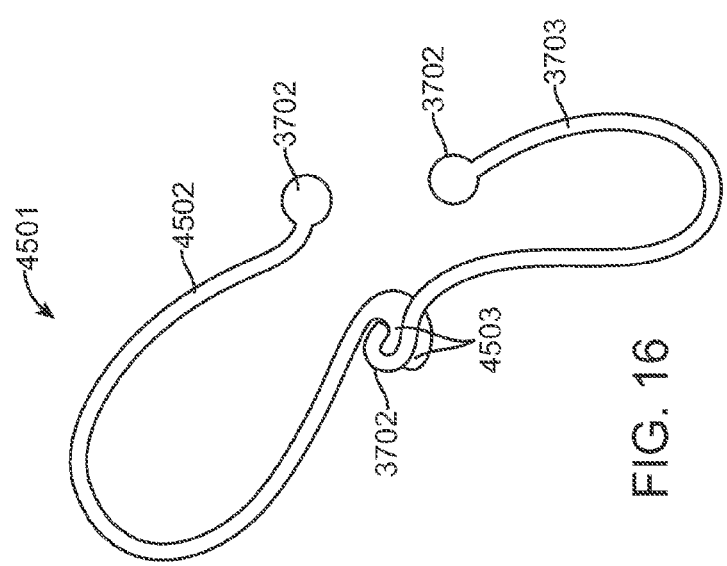
FIG. 16 illustrates a device configuration that is coupled to a second device.

FIG. 16 illustrates a system of one or more devices that can be hooked together 4501. The device 3703 is configured such that it terminates on both ends, for example, with blunt ball shaped ends 3702. The device 4502 is terminated on one end with an open cup and slot shape 4503 that allows the devices to be coupled together. These devices may be delivered together or coupled in-situ. Devices may be installed into a single duct in the lung or in different locations that may be linked together.

Figure 17:
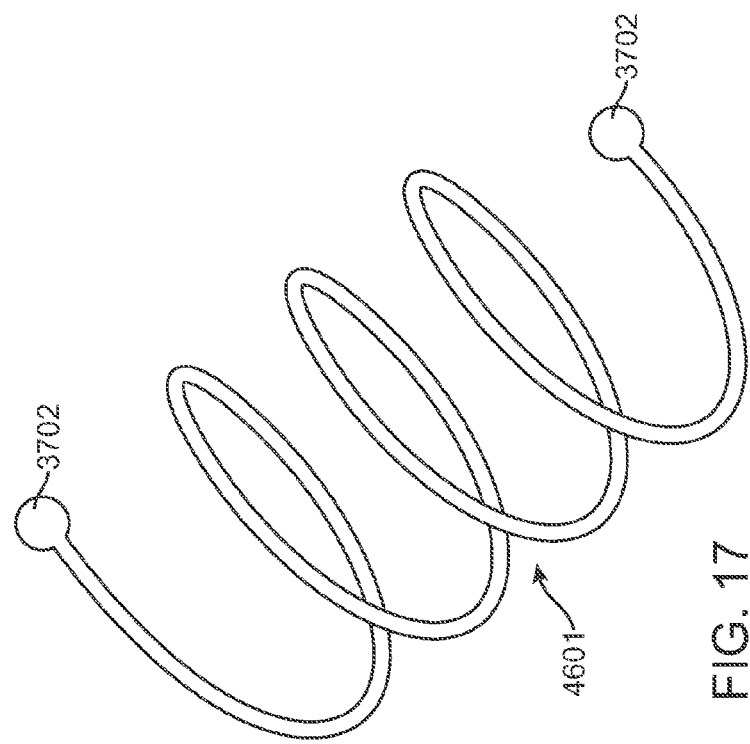
FIG. 17 illustrates a device configuration in a coil shape.

FIG. 17 illustrates another three dimensional device 4601 made in the form of a coil with ball terminations 3702.

Figure 18:
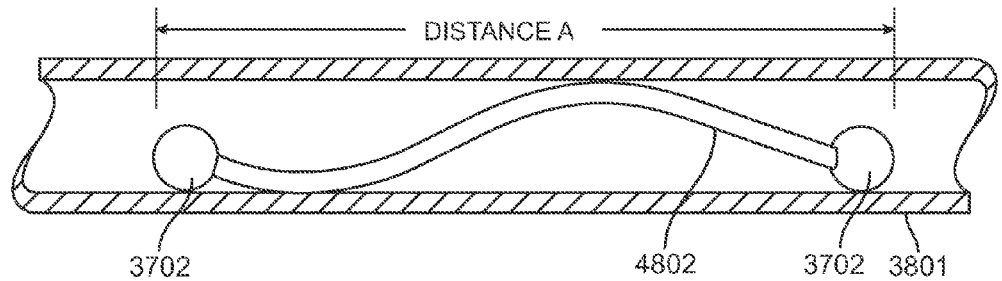
FIG. 18 illustrates a length change from delivery to deployed.
Figure 19:
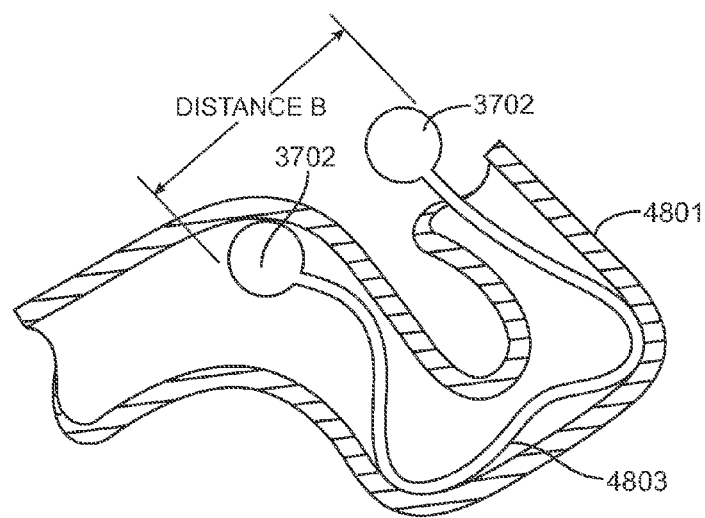
FIG. 19 illustrates a system with bronchoscope, catheter, dilator, wire and wire steering handle.

FIGS. 18 and 19 illustrate how the device length is reduced when the device is deployed in-situ. The device shown in the delivery configuration 4802 in FIG. 18 is also shown in the deployed configuration 4803 in FIG. 19. The distance A between the device ends 3702 is large while the device is constrained by the constraining cartridge device 3801. Distance A is similar when the device is constrained by a loading cartridge, catheter or bronchoscope. FIG. 19 shows the same device in a deployed configuration 4803 in an airway 4801 that has been deformed by the shape recovery of the implant device. FIG. 19 shows that the distance B between the device ends 3702 is substantially shorter after the device is deployed.

As with previous embodiments, the embodiments depicted in FIGS. 8-19 are adapted and configured to be delivered to a lung airway of a patient in a delivery configuration and to change to a deployed configuration to bend the lung airway. The devices are characterized in that the devices have a delivery configuration that is resiliently bendable into a plurality of shapes, such as the ones depicted in the Figures. The design of the devices can be such that strain relief is facilitated on both ends of the device. Further the ends of the device in either the delivery or deployed state are more resilient.

The devices can have any suitable length for treating target tissue. However, the length typically range from, for example, 2 cm to 10 cm, usually 5 cm. The diameter of the device can range from 1.00 mm to 3.0 mm, preferably 2.4 mm. The device is used with a catheter which has a working length of 60 cm to 200 cm, preferably 90 cm.

In operation the devices shown in FIGS. 8-19 are adapted and configured to be minimally invasive which facilitates easy use with a bronchoscope procedure. Typically, there is no incision, and no violation of the pleural space of the lung during deployment. Furthermore, collateral ventilation in the lung does not affect the effectiveness of the implanted device. As a result, the devices are suitable for use with either homogeneous and heterogeneous emphysema.

Each of the devices depicted in FIGS. 8-19 are adapted and configured to impart bending force on lung tissue. For example, a spring element can be provided, as illustrated in FIG. 11 that imparts bending force on lung tissue. The implantable spring element that can be constrained into a shape that can be delivered to a lung airway and unconstrained to allow the element to impart bending force on the airway to cause the airway to be bent.

Embodiments of the lung volume reduction system can be adapted to provide an implant that is constrained in a first configuration to a relatively straighter delivery configuration and allowed to recover in situ to a second configuration that is less straight configuration. Devices and implants can be made, at least partially, of spring material that will fully recover after having been strained at least 1%, suitable material includes a metal, such as metals comprising Nickel and Titanium. In some embodiments, the implant of the lung volume reduction system is cooled below body temperature in the delivered configuration. In such an embodiment, the cooling system can be controlled by a temperature sensing feedback loop and a feedback signal can be provided by a temperature transducer in the system. The device can be configured to have an Af temperature adjusted to 37 degrees Celsius or colder. Additionally, at least a portion of the metal of the device can be transformed to the martensite phase in the delivery configuration and/or can be in an austenite phase condition in the deployed configuration.

Lung volume reduction systems, such as those depicted in FIGS. 8-19, comprise an implantable device that is configured to be deliverable into a patient's lung and which is also configured to be reshaped to make the lung tissue that is in contact with the device more curved. Increasing the curvature of the tissue assists in reducing the lung volume of diseased tissue, which in turn increases the lung volume of healthier tissue. In some instances, the devices are configured to be reshaped to a permanent second configuration. However, as will be appreciated by those skilled in the art, the devices can also be adapted and configured to have a first shape and is configured to be strained elastically to a deliverable shape.

As will be appreciated by those skilled in the art, the devices illustrated in FIGS. 8-19 are can be configured to be deliverable into a patient's lung and configured to reshape lung tissue while allowing fluid to flow both directions past the implant.

Figure 20:
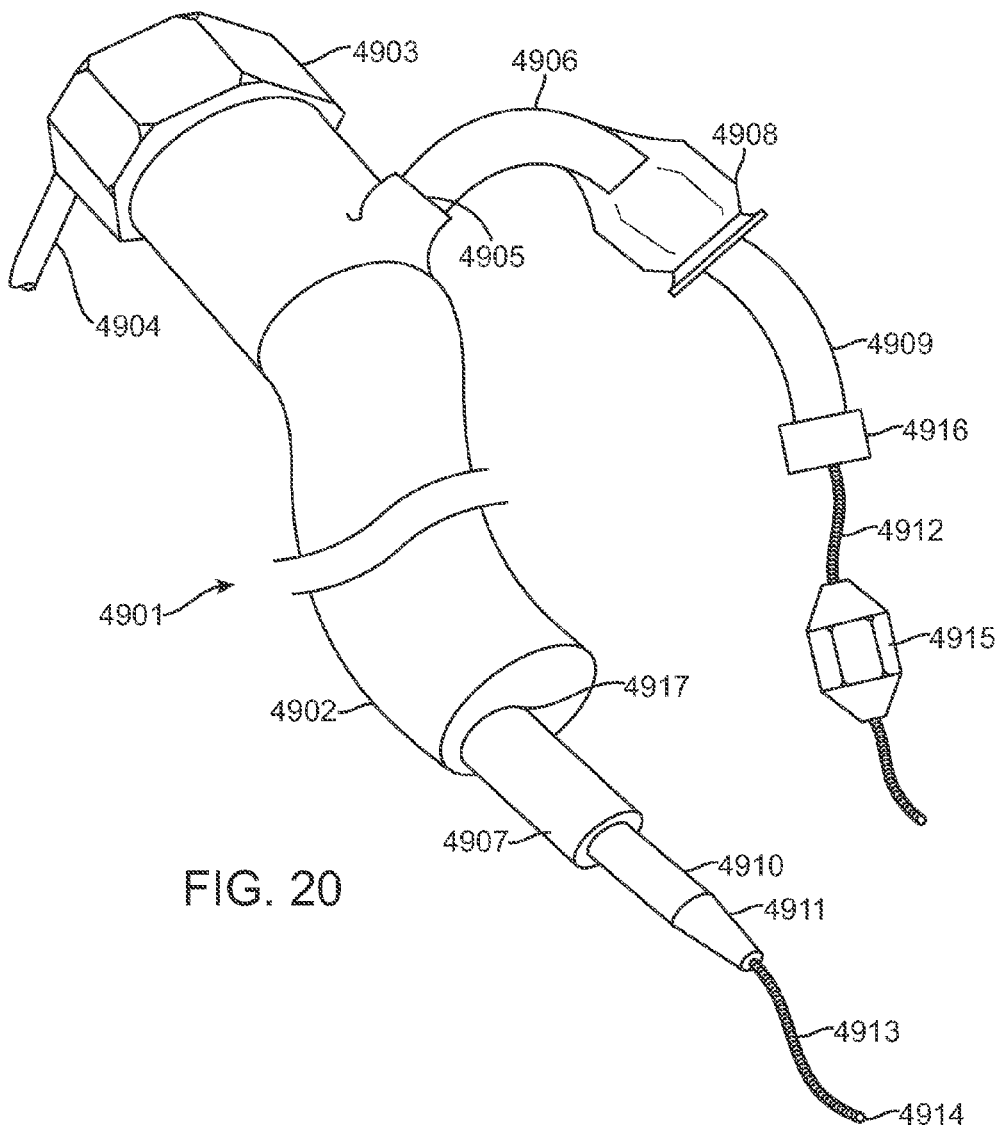
FIG. 20 illustrates a system in an airway with device ready to deliver.

FIG. 20 illustrates a system 4901 that may be used to deliver the implant device. The many components of the system may be needed to guide the bronchoscope 4902 to a site that is appropriate for implant delivery. The airway guide wire has a distal floppy section 4913 that can be steered into any desired airway by rotating the slight curve at the distal tip to the appropriate trajectory at airway bifurcations. To apply torque to the wire, devices such as a locking wire steering handle 4915 may be attached to the proximal end of the wire 4912. The wire tip may be blunt such as the ball tip shown 4914. In some embodiments, the wire may be adapted and configured to pass through a dilator catheter 4909 that is shaped to provide a smooth diameter transition from the wire diameter to the delivery catheter 4906 diameter. The distal tip of the dilator 4910 should be tapered 4911 as shown. The dilator prevents the open end of the delivery catheter 4906 to dig into lung tissue in an unintended way. The dilator hub 4916 may be made as a Y-fitting to allow the user to couple a syringe and inject radiopaque dye through the dilator lumen to increase the visibility of the airways, which facilitates the use of an x-ray guidance system, such as fluoroscopy or computed tomography. The delivery catheter may be used without the wire and dilator. The catheter 4906 is designed to constrain the device in a deliverable shape while it is advanced through the system and into the patient. The distal end 4907 may be configured from a floppier polymer or braid than the proximal end 4906 and the distal tip may further include a radiopaque material associated with the tip, either integral or adjacent, to identify the position of the tip relative to other anatomical locations, such as bones. Providing one or more radiopaque markers facilitates using x-ray guidance system to position the distal end of the device in situ relative to a target anatomy. The proximal termination of the delivery catheter 4908 may further be adapted to incorporate a lockable hub to secure the loading cartridge 3801 with a smooth continuous lumen. The delivery catheter 4906 is shown introduced into the bronchoscope side port 4905 and out the distal end of the scope 4917. A camera 4903 is shown attached to the end of the scope with a cable 4904, or other delivery mechanism, to transmit the image signal to a processor and monitor. The loading cartridge, delivery catheter, dilator, guide wire and wire steering handle may be made from any material identified in this specification or materials well known to be used for similar products used in the human vascular tract by radiologists.

Figure 21:
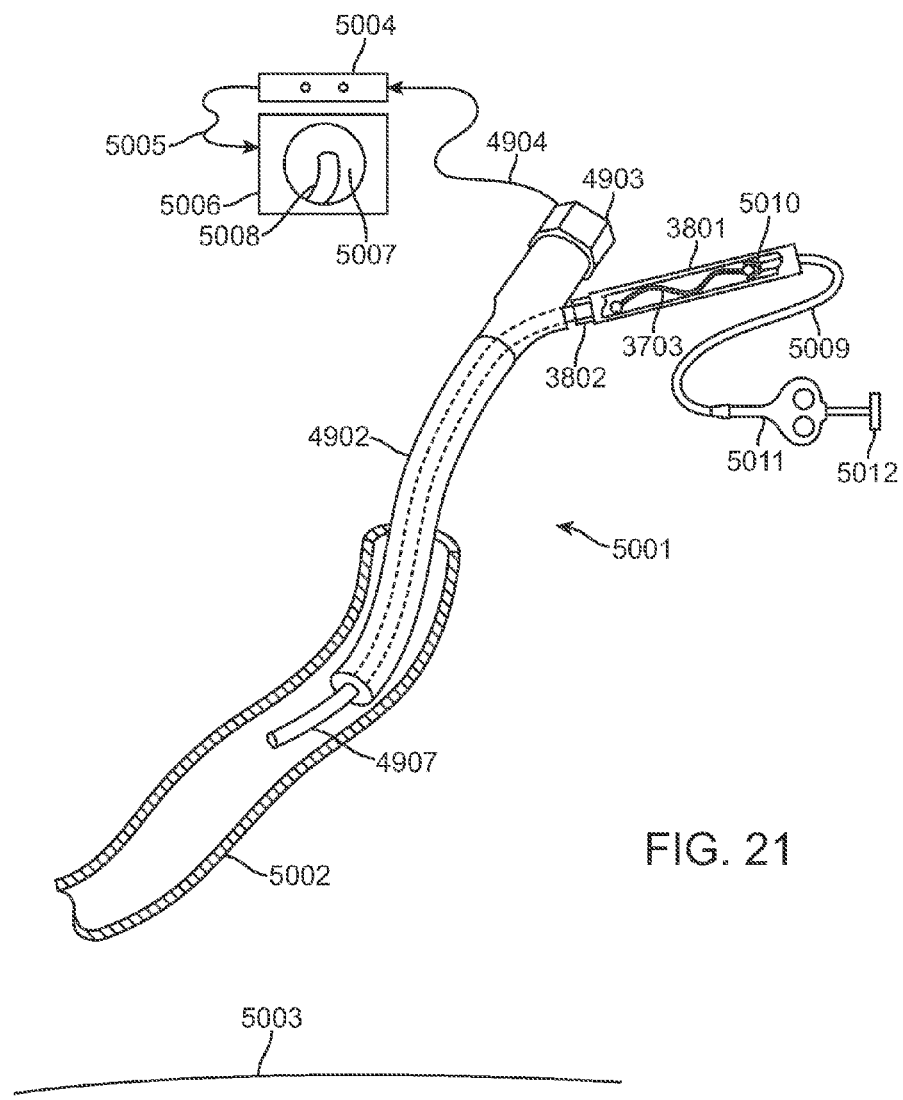
FIG. 21 illustrates a system in an airway delivering the device.

FIG. 21 illustrates a delivery system 5001 that has been placed into a human lung. The bronchoscope 4902 is in an airway 5002. The scope camera 4903 is coupled to a video processor 5004 via a cable 4904. The image is processed and sent through a cable 5005 to a monitor 5006. The monitor shows a typical visual orientation on the screen 5007 of a delivery catheter image 5008 just ahead of the optical element in the scope. The distal end of the delivery catheter 4907 protrudes out of the scope in an airway 5002 where the user will place an implant device 3703. The implant 3703 is loaded into a loading cartridge 3801 that is coupled to the proximal end of the delivery catheter via locking hub connection 3802. A pusher grasper device 5009 is coupled to the proximal end of the implant 3703 with a grasper coupler 5010 that is locked to the implant using an actuation plunger 5012, handle 5011 and pull wire that runs through the central lumen in the pusher catheter. By releasably coupling the pusher to the implant device, the user may advance the implant to a position in the lung in a deployed configuration. The user can survey the implant placement position and still be able to retrieve the implant back into the delivery catheter, with ease, if the delivery position is less than ideal. The device has not been delivered and the bottom surface of the lung 5003 is shown as generally flat and the airway is shown as generally straight. These are both anatomically correct for a lung with no implant devices. If the delivery position is correct, the user may actuate the plunger 5012 to release the implant into the patient.

Figure 22:
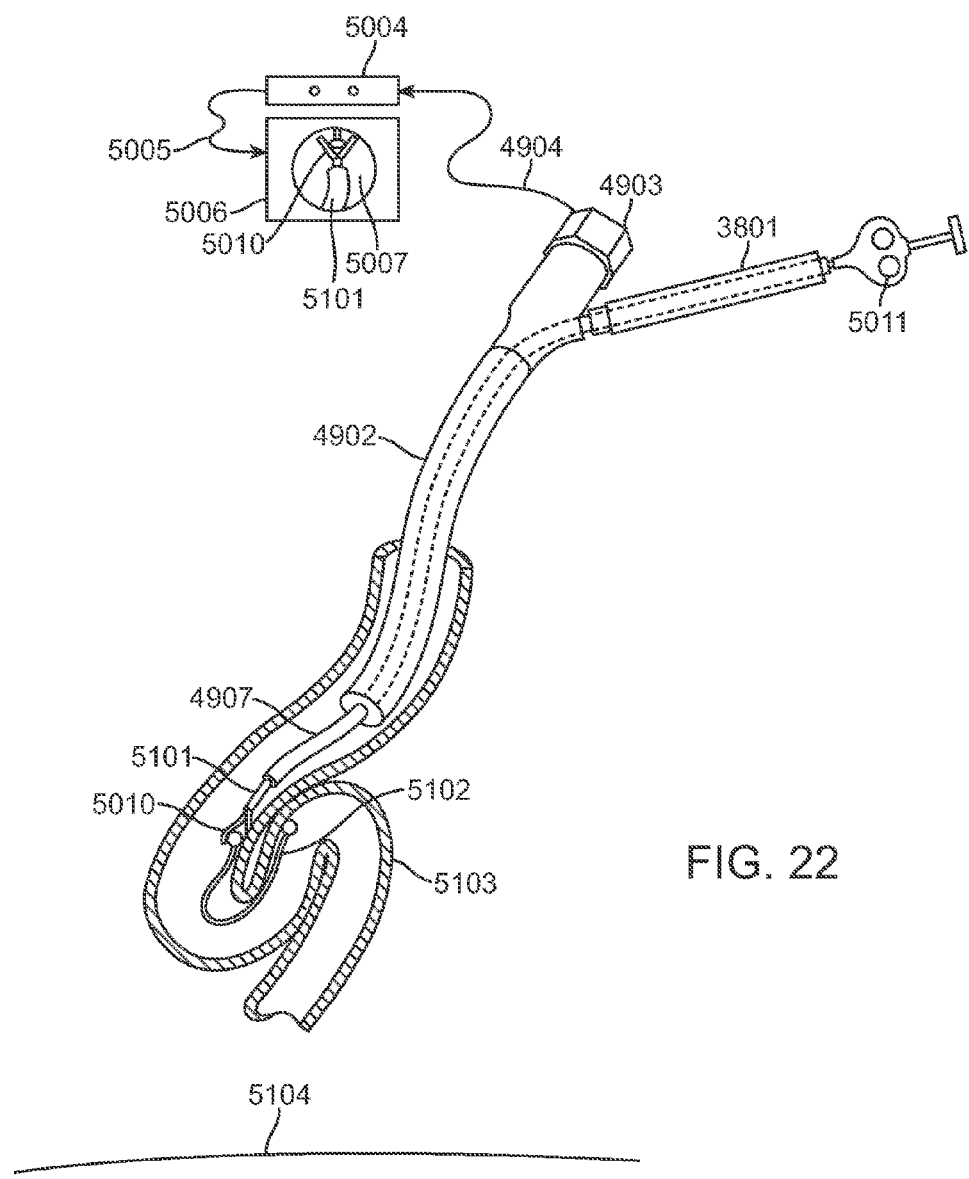
FIG. 22 illustrates a system in an airway with the device delivered.

FIG. 22 illustrates generally the same system after the implant has been deployed into the airway 5103. The implant 5102 and pusher 5101 has been advanced through the delivery catheter 4907 to a location distal to the scope 4902. The pusher grasping jaws 5010 are still locked onto the proximal end of the implant 5102 but the implant has recovered to a pre-programmed shape that has also bent the airway 5103 into a folded configuration. By folding the airway, the airway structure has been effectively shortened within the lung. Since the airways are well anchored into the lung tissue, the airway provides tension on the surrounding lung tissue which is graphically depicted by showing the pulled (curved inward) floor of the lung 5104. The image from the camera 4903 is transmitted through the signal processor 5004 to the monitor 5006 to show the distal tip of the delivery catheter 5101, distal grasper of the pusher 5010 and proximal end of the implant 3703. The grasper may be used to locate, couple to and retrieve devices that have been released in the patient. It is easy to envision, with reference to FIG. 22, how the implant performs work on the airways and lung tissue without blocking the entire lumen of the airway. This is a benefit in that fluid or air may pass either way through the airway past the implant device.

Figure 23:
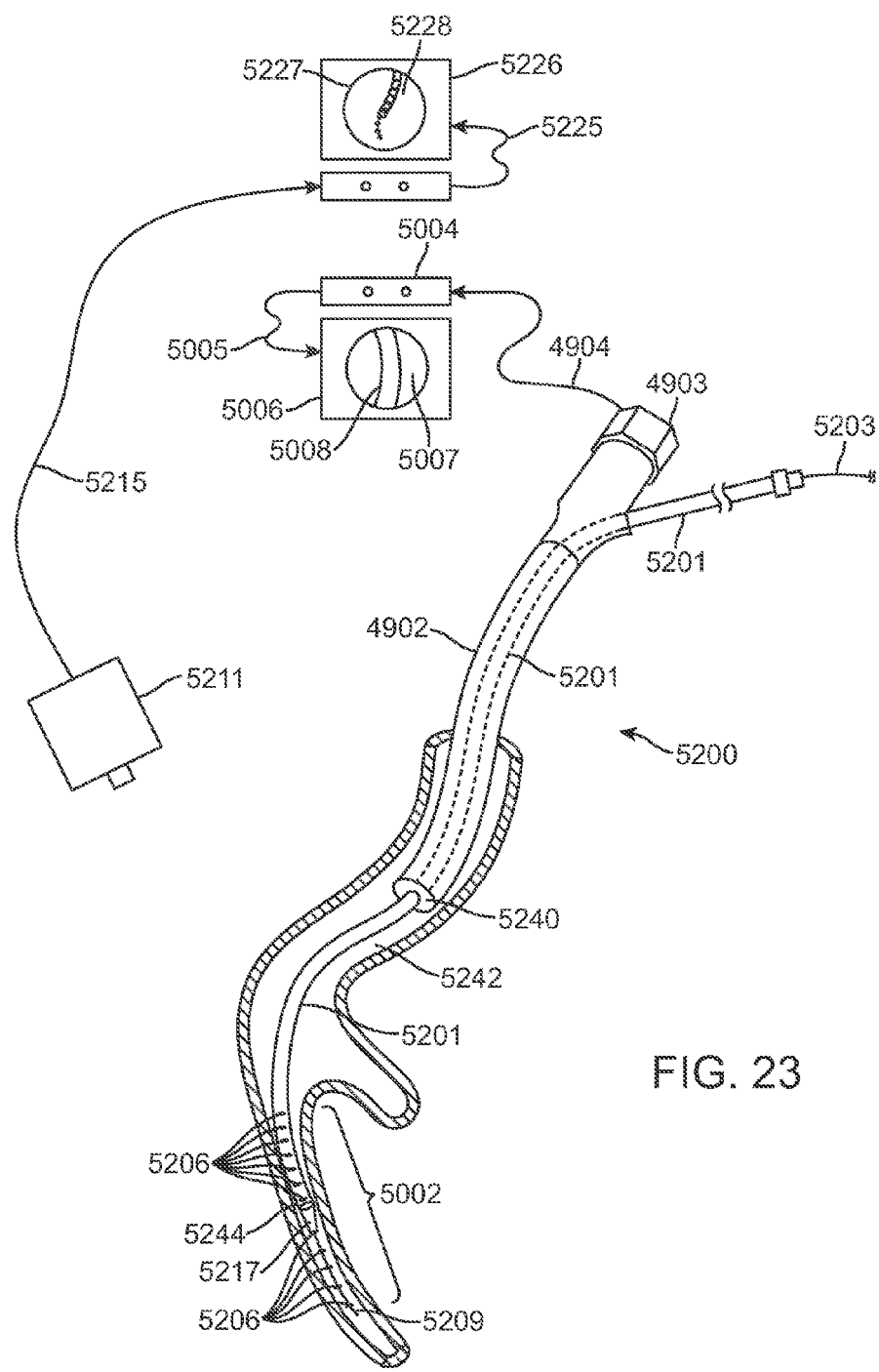
FIG. 23 illustrates a system with a bronchoscope, catheter, dilator, and guidewire.

FIG. 23 illustrates delivery system 5200 as placed into a patient body, and particularly into a human lung. Delivery system 5200 may be generally similar to system 4901 or 5001 described above. The distal end 5240 of bronchoscope 4902 extends into an airway system toward an airway portion or axial region 5002. The scope camera 4903 is coupled to a video processor 5004 via a cable 4904. The image is processed and sent through a cable 5005 to a monitor 5006. Monitor 5006 shows on screen 5007 a portion of a delivery catheter image 5008 just ahead of the optical image capture element in the scope. In some embodiments, the scope may be constrained by a relatively large cross-section to advancement only to a "near" region of the lung adjacent the major airways. Hence, the optical image has a viewfield that extends only a limited distance along the airway system, and it will often be desirable to implant some or all of the implant beyond a field of view 5242 of scope 4902.

Guidewire 5203 is threaded through bronchoscope 4902 and through the airway system to (and through) airway 5002. Guidewire 5203 has a cross-section significantly smaller than that of the scope, and a distal end 5209 of the guidewire 5203 may be angled as described above to facilitate steering. A fluoroscopic system, an ultrasound imaging system, an MRI system, or some other remote imaging modality having a remote image capture device 5211 allows guidance of the guidewire so that the guidewire and/or delivery catheter 5201 can be advanced beyond the viewing field of bronchoscope 4902. In some embodiments, the guidewire may be advanced under remote image guidance without the use of a scope. Regardless, the guidewire can generally be advanced well beyond the near lung, with the distal end of the guidewire often being advanced through the mid-lung to the small airways of the far lung. A distal end 5244 of laterally flexible delivery catheter 5201 can then be advanced through the lumen within bronchoscope 4902 and over guidewire 5203.

The distal portion of guidewire 5203 is provided with indicia of length 5206, the indicia indicating distances along the guidewire from distal end 5209. The indicia may comprise scale numbers or simple scale markings, and distal end 5244 of catheter 5201 may have one or more corresponding high contrast markers, with the indicia of the guidewire and the marker of the catheter typically visible using the remote imaging system. Hence, remote imaging camera 5211 can identify, track or image indicia 5206 and thus provide the length of the guidewire portion extending between (and the relative position of) the distal end of delivery catheter 5201 and the distal end 5209 of guidewire 5203. Indicia of length 5206 may, for example, comprise radiopaque or sonographic markers and the remote imaging modality may comprise, for example, an x-ray or fluoroscopic guidance system. Note that some of the indicia of the guidewire are schematically shown through the distal portion of the catheter in FIG. 23. Indicia of length 5206 thus facilitate using a guidance system to measure a length of airway 5002 or other portion of the airway system beyond the field of view of the scope, thereby allowing an implant of appropriate length to be selected.

Remote imaging modality 5221 is coupled to imaging processor 5224 via cable 5215. Imaging processor 5224 is coupled to a monitor 5226 which displays an image 5228 on screen 5227. Image 5228 shows the indicia of lengths 5205 and 5206 of delivery catheter 5201 and guidewire 5203, respectively. A dilator 5217 may be advanced through the lumen of the catheter so that the distal end of the dilator extends from the distal end of delivery catheter 5201 when the catheter is being advanced. Dilator 5217 atraumatically expands openings of the airway system as delivery catheter 5201 advances distally. Dilator 5217 tapers radially outwardly proximal of the distal tip of guidewire 5203, facilitating advancement of the catheter distally to or through the mid-lung toward the far lung. Once the catheter has been advanced to the distal end of airway portion 5002 targeted for delivery (optionally being advanced over the guidewire as far as the cross-section of the catheter allows the catheter to be safely extended), the length of the airway is measured and the dilator 5217 and guidewire 5203 are typically withdrawn proximally from deliver catheter 5201 so as to provide an open lumen of the delivery catheter from which a lung volume reduction device can be deployed.

In some embodiments, an implant is deployed in a straight configuration with the use of a catheter, e.g., catheter 5201, to contain it in a generally straight shape. Alternative embodiments may use the working lumen of the bronchoscope directly so that the bronchoscope is used as a delivery catheter. Upon removal of the constraining catheter, the implant recoils to a deployed shape that can be easily identified by the fact that the distance from one end to the second is reduced. The proximal end of the implant may be grasped, e.g., with pusher grasper device 5009, and held so that the distal end of the implant remains engaged against the desired airway tissue as the length of the implant is progressively unsheathed (by withdrawing the catheter proximally). High tensile forces might be generated between the distal portion of the implant and the airway tissue if the proximal end of the implant is held at a fixed location throughout deployment, as the implant is biased to recoil or bring the ends together when released. Hence, it can be advantageous to allow the proximal end of the implant to advance distally during release, rather than holding the implant from recoiling, as these forces may be deleterious. For example, the distance and tissue thickness between the distal end of the implant and the lung surface is short, there may be little strain relief on the tissue and the risk of rupture may be excessive. Additionally, the implant might otherwise tend to foreshortened after it is released by the grasper. When foreshortening occurs, the proximal end of the implant may travel distally beyond the viewing field of the bronchoscope and the user can have difficulty retrieving the implant reliably. Thus, an implant having a length longer than that of the target axial region may be selected to be deployed in some cases. Implants having a length of at least 10% more, preferably about 20% more, than the measured target axial region may be selected.

Figure 24A:
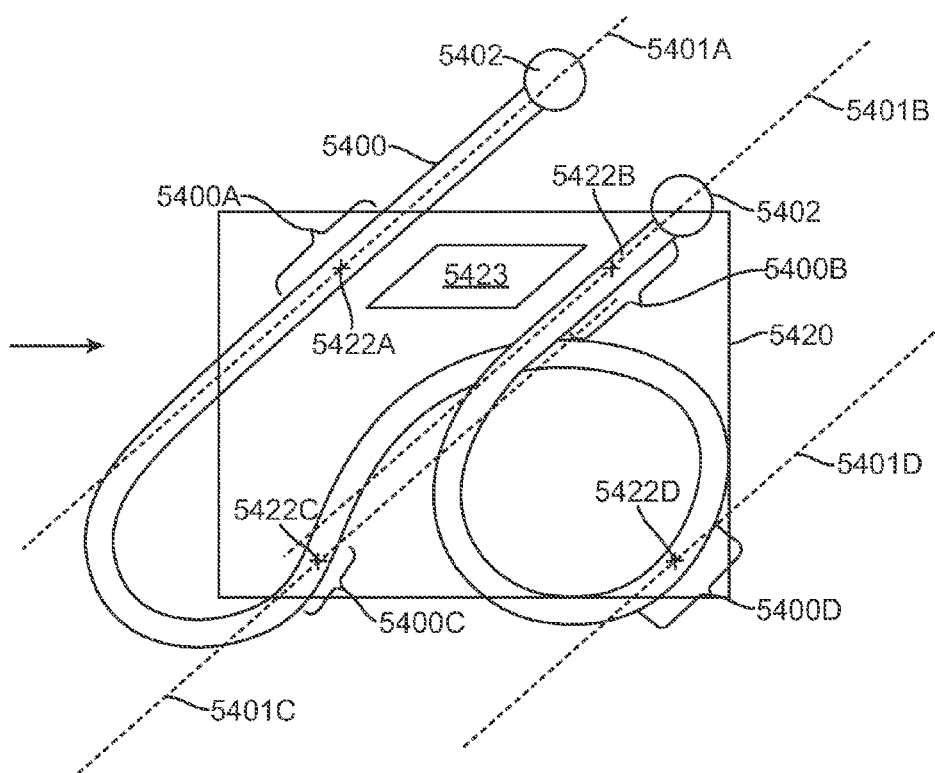
FIGS. 24A-24C illustrate lateral compression of tissue between portions of the deployed device.

FIG. 24A shows an implant 5400 for treating an airway of the lung. Implant 5400 comprises an elongate body having a first or proximal implant portion 5400A and a second or distal implant portion 5400B. Implant 5400 further comprises a third implant portion 5400C and a fourth implant portion 5400D between proximal portion 5400A and distal portion 5400B. First portion 5400A of implant 5400 defines a first local axis 5401A. Second portion 5400B defines a second local axis 5401B. Third portion 5400C defines a third local axis 5401C. Fourth portion 5400D defines a fourth local axis 5401D, with the local axes being disposed along the axis of the implant between curves of the implanted device. An elongate lateral surface of the implant can be seen to extend along the overall axis of the device (including the local axes), presenting an elongate bearing surface to engage and press against the surrounding airway. The ends of implant 5400 are formed into rounded shapes that engages a luminal surface with an autramatic surface area shown in the form of balls 5402 to minimize perforation through the airway luminal wall. The balls may be made by melting back a portion of implant 5400, however, they may be additional components that are welded, pressed or glued onto the ends of implant 5400.

Figure 24B:
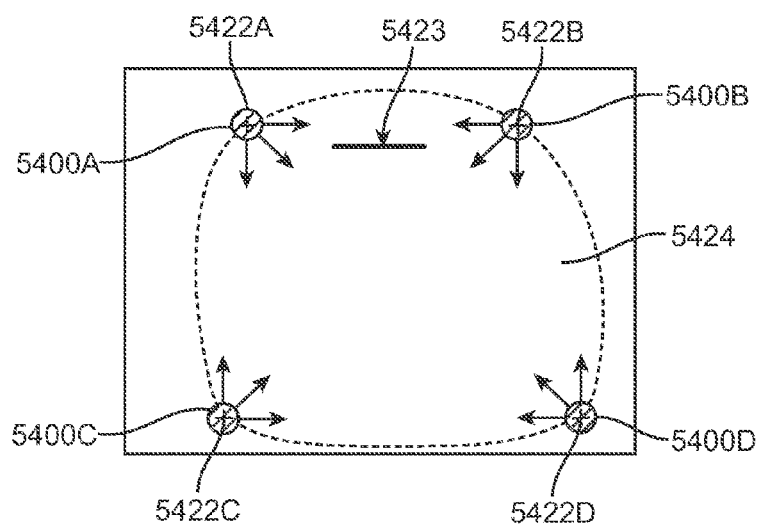

As shown in FIGS. 24A-B, first portion 5400A, second portion 5400B, third portion 5400C, and fourth portion 5400D may traverse a plane 5420, and FIG. 24B illustrates the orientation of compressive forces applied by the local portions of the elongate body in plane 5420. First portion 5400A may intersect plane 5420 at a first point 5422A. Second portion 5400B may intersect plane 5420 at a second point 5422B. Third portion 5400C may intersect plane 5420 at third point 5422C. Fourth portion 5400D may intersect plane 5420 at fourth point 5422D. Intermediate portions 5425 of the elongate body disposed between portions 5400A, 5400B, 5400C, and 5400D may be biased so that when implant 5400 is placed in an airway in a straight configuration, and when implant 5400 bends from the straight configuration to a bent configuration, first portion 5400A, second portion 5400B, third portion 5400C, and/or fourth portion 5400D are urged toward each other. More specifically, and looking at just two of the portions as shown in FIGS. 24A and 24B, first portion 5400A and second portion 5400B will often define a surface therebetween, such as compression plane 5423 (particularly where the portions are relatively flat). The first and second portions compress tissue disposed between them and near compression plane 5423, so that an implant that remains substantially planer can compress a volume of tissue. However, by also compressing tissue using portions of the elongate body that are significantly offset from compression plane 5423 (such as third portion 5400C and forth portion 5400D), a larger volume of lung tissue may be compressed. Compressed area 5424 may be representative of a cross-section of the compressed volume of lung tissue, showing how the use of additional portions of the implant that are not co-planar can enhance compression efficacy. While the above description references a compression plane for simplicity, as can be understood with reference to the illustrations of the three dimensional implants of FIGS. 5D, 10-13, 17, and the like, the implant can be configured with shapes that compress roughly spherical volumes, roughly cylindrical volumes, or other desired shapes.

Figure 24C:
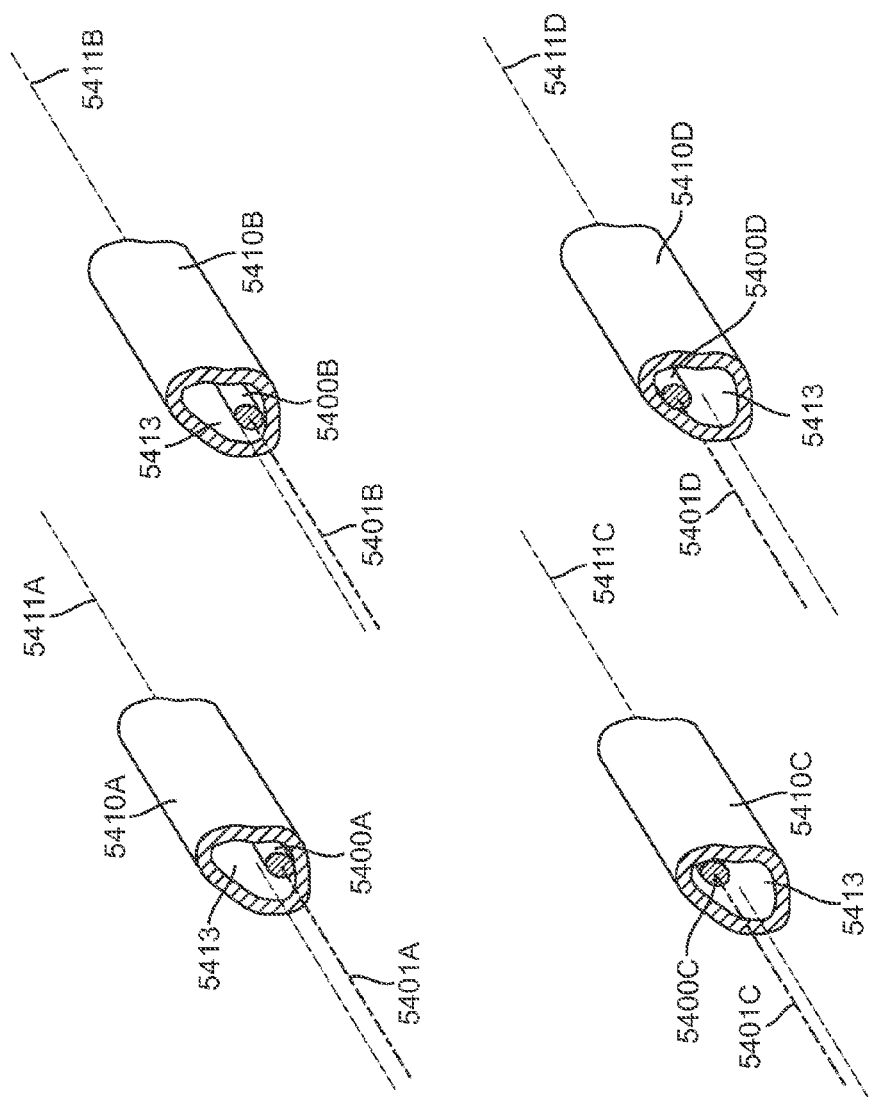

FIG. 24C shows implant 5400 placed into an airway, with only portions of the implant and airway shown for simplicity. The airway comprises a first proximal airway axial region 5410A, a second distal airway axial region 5410B, and a third airway axial region 5410C and a fourth airway axial region 5410D between the first airway axial region 5410A and second airway axial region 5410D. First airway axial region 5410A defines a first local airway axis 5411A. Second airway axial region 5410B defines a second local airway axis 5411B. Third airway axial region 5410C defines a third local airway axis 5411C. Fourth airway axial region 5410D defines a fourth local airway axis 5411D. First airway axial region 5410A, second airway axial region 5410B, third airway axial region 5410C, and fourth airway axial region 5410D each have inner luminal surfaces 5413. First airway axial region 5410A, second airway axial region 5410B, third airway axial region 5410C, and fourth airway axial region 5410D are coupled together axially. First implant portion 5400A of implant 5400 can engage with first airway axial region 5410A. Second implant portion 5400B of implant 5400 can engage with second airway axial region 5410B. Third implant portion 5400C of implant 5400 can engage with third airway axial region 5410C. Fourth implant portion 5400D of implant 5400 can engage with fourth airway axial region 5410D. Implant 5400 can urge first airway axial region 5410A, second airway axial region 5410B, third airway axial region 5410C, and/or fourth airway axial region 5410D laterally toward each other by having respective implant portions urging against inner luminal surfaces 5413, thereby imposing a bend in the airway system and compressing the volume of lung tissue disposed between first airway axial region 5410A, second airway axial region 5410B, third airway axial region 5410C, and/or fourth airway axial region 5410D. The compressed volume of lung tissue may be sufficiently large and may be compressed sufficiently to increase tension in an uncompressed volume of the lung such that lung function of the lung is increased.

By using a longer implant, the proximal end of the implant can also be fed into the airway while the potential energy of the implant is being freed to apply work on the lung tissue (while the catheter is being pulled off of the implant). The lung airways can be distorted so the airway cross section is pushed to a more oval shape. Longer implants can tend to zigzag back and forth across the airway lumen so that implants that are significantly longer than the measured airway length can be introduced. For example, a 150 mm long (arc length) implant can be deployed into a 100 mm long airway. The greater length of the implant may minimize the uncontrolled recoil that may cause the proximal end to be lost in the patient upon release. Greater implant length can also allow the user to feed the implant into the patient while the catheter is removed without over stressing the lung tissue. Additionally, should foreshortening of the longer implant occur, the proximal end of the implant can still remain within the viewing field of the bronchoscope and the user can thus retain the ability to retrieve the implant reliably. It should be understood that the length of the implant relative to the diameter of the airway may be much greater than the schematic illustrations of the figures, that the implant may have more complex three dimensional curvature to effect volumetric compression of the lung tissue, and the like.

As will be appreciated by those skilled in the art, the device can be manufactured and deployed such that it is deliverable through a bronchoscope. When actuated, the device can be adapted and configured to bend or curl which then distorts lung tissue with which the device comes in contact. Lung tissues that may be beneficially distorted by the device are airways, blood vessels, faces of tissue that have been dissected for introduction of the device or a combination of any of these. By compressing the lung tissue, the device can result in an increase in elastic recoil and tension in the lung in at least some cases. Additionally, in some instances, lung function can be at least partially restored regardless of the amount of collateral ventilation. Further, the diaphragm may, in some instances, move up once greater tension is created which enables the lung cavity to operate more effectively.

Devices according to the invention have a small cross-section, typically less than 10F. The flexibility of the device prior to deployment facilitates advancement of the device through the tortuous lung anatomy. Once deployed, the device can remain rigid to hold and maintain a tissue deforming effect. Further, the device design facilitates recapture, de-activation and removal as well as adjustment in place.

Candidate materials for the devices and components described herein would be known by persons skilled in the art and include, for example, suitable biocompatible materials such as metals (e.g. stainless steel, shape memory alloys, such a nickel titanium alloy (nitinol), titanium, and cobalt) and engineering plastics (e.g. polycarbonate). See, for example U.S. Pat. No. 5,190,546 to Jervis for Medical Devices Incorporating SIM Memory Alloy Elements and U.S. Pat. No. 5,964,770 to Flomenblit for High Strength Medical Devices of Shape Memory Alloy. In some embodiments, other materials may be appropriate for some or all of the components, such as biocompatible polymers, including polyetheretherketone (PEEK), polyarylamide, polyethylene, and polysulphone. As noted above, the structures of the implants may also comprise and/or be coated with a hydrophilic polymer, with the polymer preferably being sufficiently hydrophilic to inhibit formation of a biofilm. Suitable hydrophilic polymers may comprise polycarbonate urethanes (PCUs) such as those used for coating cardiac pacemaker leads and the like. Exemplary PCUs include relatively high durometer PCUs such as a 55D PCU, as is commercially available from a variety of sources.

Polymers and metals used to make the implant and delivery system could alternatively be coated with materials to prevent the formation and growth of granular tissue, scar tissue and mucus. Many of the drugs used with stent products to arrest hyperplasia of smooth muscle cells in blood vessels after deploying metallic stents will work very well for these devices. Slow release drug eluting polymers or solvents may be used to regulate the release of drugs that include any substance capable of exerting a therapeutic or prophylactic effect for a patient. For example, the drug could be designed to inhibit the activity of smooth muscle cells. It can be directed at inhibiting abnormal or inappropriate migration and/or proliferation of smooth muscle cells to inhibit tissue mass buildup. The drug may include small molecule drugs, peptides or proteins. Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin$_1$, actinomycin X$_1$, and actinomycin C$_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co. of Stamford, Conn.), docetaxel (e.g. Taxotere®, from Aventis S. A. of Frankfurt, Germany) methotrexate, azathioprine, vincristine, vinblastine, fluorouracil, doxorubicin hydrochloride (e.g. Adriamycin® from Pharmacia & Upjohn of Peapack N.J.), and mitomycin (e.g. Mutamycin® from Bristol—Myers Squibb). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hh/IIIa platelet membrane receptor antagonist antibody, recombinant hirudin, and thrombin inhibitors such as Angiomax™ (Biogen, Inc. of Cambridge, Mass.). Examples of such cytostatic or antiproliferative agents include angiopeptin, angiotensin converting enzyme inhibitors such as captopril (e.g. Capoten® and Capozide® from Bristol-Myers Squibb), cilazapril or Hsinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis of New York, N.Y.), 40-O-(3-hydroxy)propyl-rapamycin, 40-O-[2-(2-hydroxy)ethoxy]ethyl-rapamycin, and 40-O-tetrazole-rapamycin.

Other polymers that may be suitable for use in some embodiments, for example other grades of PEEK, such as 30% glass-filled or 30% carbon filled, provided such materials are cleared for use in implantable devices by the FDA, or other regulatory body. The use of glass filled PEEK would be desirable where there was a need to reduce the expansion rate and increase the flexural modulus of PEEK for the instrument Glass-filled PEEK is known to be ideal for improved strength, stiffness, or stability while carbon filled PEEK is known to enhance the compressive strength and stiffness of PEEK and lower its expansion rate. Still other suitable biocompatible thermoplastic or thermoplastic polycondensate materials may be suitable, including materials that have good memory, are flexible, and/or deflectable have very low moisture absorption, and good wear and/or abrasion resistance, can be used without departing from the scope of the invention. These include polyetherketoneketone (PEKK), polyetherketone (PEK), polyetherketoneetherketoneketone (PEKEKK), and polyetheretherketoneketone (PEEKK), and generally a polyaryletheretherketone. Further other polyketones can be used as well as other thermoplastics. Reference to appropriate polymers that can be used in the tools or tool components can be made to the following documents, all of which are incorporated herein by reference. These documents include: PCT Publication WO 02/02158 A1, to Victrex Manufacturing Ltd. entitled Bio-Compatible Polymeric Materials; PCT Publication WO 02/00275 A1, to Victrex Manufacturing Ltd. entitled Bio-Compatible Polymeric Materials; and PCT Publication WO 02/00270 A1, to Victrex Manufacturing Ltd. entitled Bio-Compatible Polymeric Materials. Still other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used as well for portions of the instrument that are desired to be radiolucent.

The implant described herein can be made of a metallic material or an alloy such as, but not limited to, cobalt-chromium alloys (e.g., ELGILOY), stainless steel (316L), "MP3SN," "MP2ON," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP2ON" are trade names for alloys of cobalt, nickel, chromium and molybdenum available from Standard Press Steel Co. of Tenkintown, Pa. "MP35N" consists of 35% cobalt, 35% nickel, 20% chromium, and 10% molybdenum. "MP2ON" consists of 50% cobalt, 20% nickel, 20% chromium, and 10% molybdenum.

The lung volume reduction devices described below may include features to:

1—Increase the support area bearing between the proximal and distal ends of the device for engagement against the tissue so that the device remains within the airway despite the chronic force of the deployed device against the wall of the airway;

2—Increase the device friction with the airway to allow the device to grip as the device is deployed. This may prevent the device from longitudinally sliding in the airway and increase effectiveness of the device at gathering the damaged lung tissue together in compression.

3-Maintain an ability to recapture the device back into the delivery catheter, or to capture the device with a grasper and successfully pull it out of the lung after deployment is complete. Many of these devices can be recaptured even when an adhesive is infused around the device during or after deployment (the adhesive ideally comprising a Pneu-Seal™ albumin-glutaraldehyde adhesive) by pulling the device out of the sealant.

4-Inflammation to the tissue may be inhibited. The materials should be biocompatible and/or generally rounded so micro motion between the device and airway don't cause an acceleration of tissue degradation.

5-Contact between the device and the airway wall may cause tissue thickening that can be beneficial. Some tissue ingrowth (stimulation of tissue growth) may thicken the tissue foundation adjacent the device so that the device is better supported.

6-Interaction between the implant device feature(s) may increase an effective support bearing area of the tissue and/or the tissue's ability to withstand a long-term force load from the implant. For example, a sealant and/or adhesive material may be injected adjacent the implant in the lung. The material may reinforce a weakened airway wall, ideally by cross-linking to the tissue of the airway wall, so as to provide an adhesive-reinforced tissue wall structure against which the implant applies tissue compression forces.

The devices (and/or components of the devices) described below may be made from any of the materials described above. These devices and their components may comprise implantable metals such as stainless steel metals, titanium, nickel titanium, chromium steels, biocompatible polymers, shape memory polymers, and/or the like. The metal components can be co-extruded with polymer coating, or otherwise coated with polymers, optionally with polymers that swell to increase size, hydrogels, resorbable polymers, or the like. Polymers that have been (or are in the future) developed for balloons may be appropriate, as well as drug eluting materials (anti-inflammatory drugs can be imbedded therein). Suitable polymers may include nylons, polyesters, the PEEK family, polysulphones, polyesters, PTFE's such as Teflon™ and expanded Teflon™ polymers from Gore, or the like. Exemplary polymers may comprise a hydrophilic polymer, with the polymer preferably being sufficiently hydrophilic to inhibit formation of a biofilm. Suitable hydrophilic polymers may comprise polycarbonate urethanes (PCUs) such as those used for coating cardiac pacemaker leads and the like. Exemplary PCUs include relatively high durometer PCUs such as a 55D PCU, as is commercially available from a variety of sources. The devices of FIG. 58 et. seq. are generally schematically shown in a straight configuration to depict the shaped device as it looks in the delivery catheter in a pre-deployed generally straightened condition. These device can generally be deployed to recover into a non-straight pre-programmed shape (for example, as described above regarding FIGS. 8-24C) that gathers up diseased lung tissue to cause lung volume reduction, and/or a reduction in a volume of the diseased tissue so as to allow expansion of the remaining functional tissue in patients with Emphysema and/or COPD.

Figure 25:
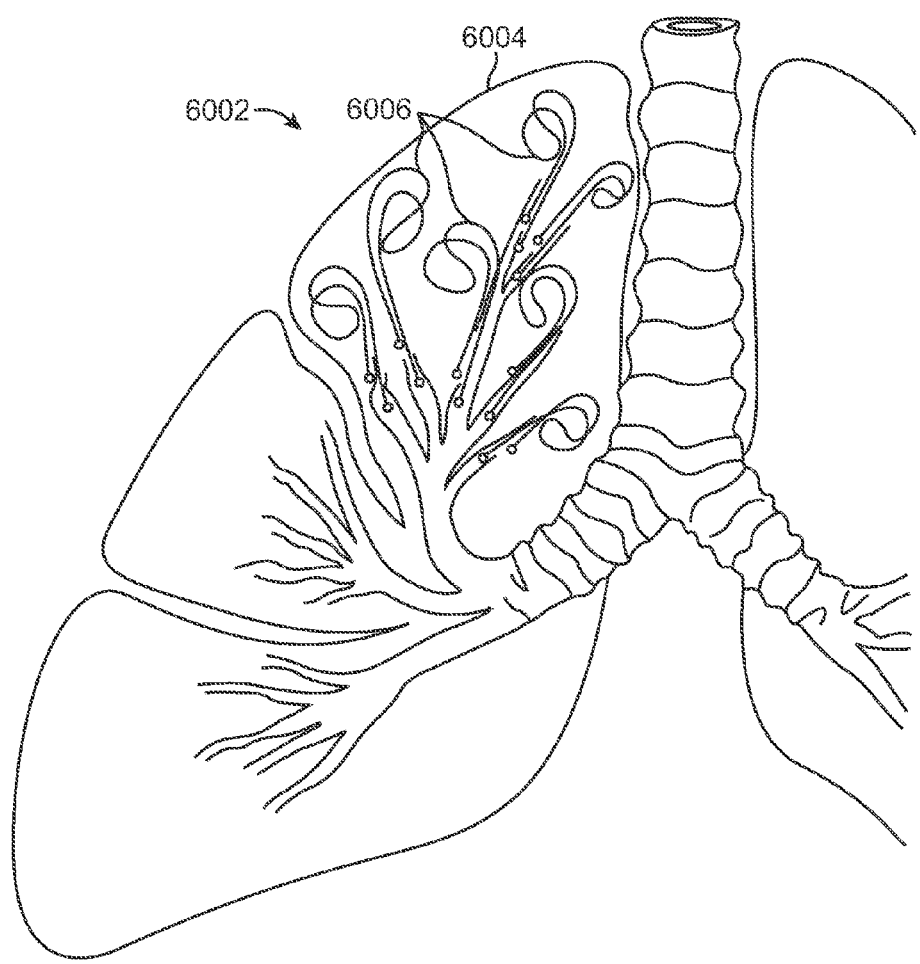
FIG. 25 schematically shows a lung that has an upper lobe treated by deployment of a plurality of devices.

FIG. 25 is a schematic illustration of a lung 6002 that has an upper lobe 6004 treated by deployment of a plurality of devices 6006, with a lobe often having between 2 and 20 devices deployed therein, optionally having between 3 and 15 devices, and in some cased between 5 and 10 devices. The devices have recovered to or near their relaxed shape and the ends of the devices include locally enlarged cross-sections in the form of rounded balls so as to help the ends of the device remain in the airways they were delivered into.

Figure 26:
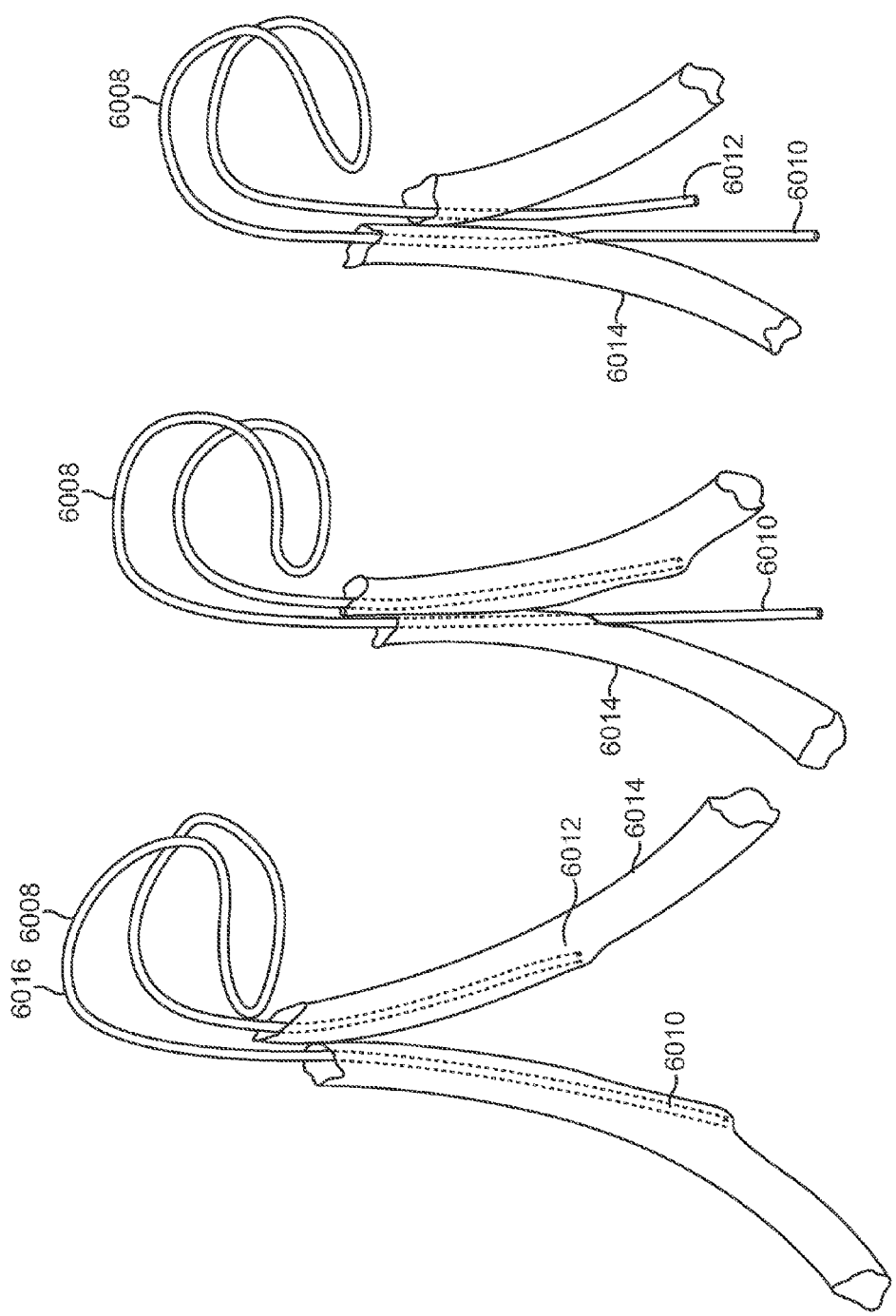
FIGS. 26A, 26B, and 26C show conditions that may be encountered several months after a device has been deployed.

Referring now to FIGS. 26A, 26B, and 26C, three conditions that may be encountered up to several months after an alternative device has been deployed are illustrated. FIG. 26A shows a device 6008 in the airway as initially placed. A first (to the left in the illustration) leg 6010 shown in the drawing may comprise a proximal portion of the device during deployment, and is longer than the second (distal) leg 6012, with the proximal leg being disposed in the more proximal (or central) portion of the airway 6014. Device 6008 comprises an elongate body comprising a wire or shaft as described above, without atraumatic ball ends or the like. The distal leg is pictured in the more distal section of the same airway, with a central portion of the airway not being shown for ease of understanding. The device was straight upon delivery and then it recovered to bend the same airway around. Generally, the airway adjacent the proximal portion or leg of the device remains relatively stationary within the lung while the airway adjacent the distal leg is more distorted by the device and is pulled toward the central lung.

FIG. 26B shows a proximal device leg 6010 that has, over time, protruded through the wall of the proximal potion of the airway 6014. This can be caused by chronic force imposed by the implant against the tissue of the airway wall, and particularly by concentrated pressure that overcomes the ability of the tissue to support the amount of force. Once again, in this embodiment the devices do not have proximal and distal ball ends. Balls at the proximal end distal ends can help prevent the adjacent axial portions of the device from extending through the airway wall, but even with such ball ends portions of the device might eventually protrude into (or even through) the wall. FIG. 26C shows the same phenomenon but with both legs 6010, 6012 protruding through the airway wall.

Figure 27:
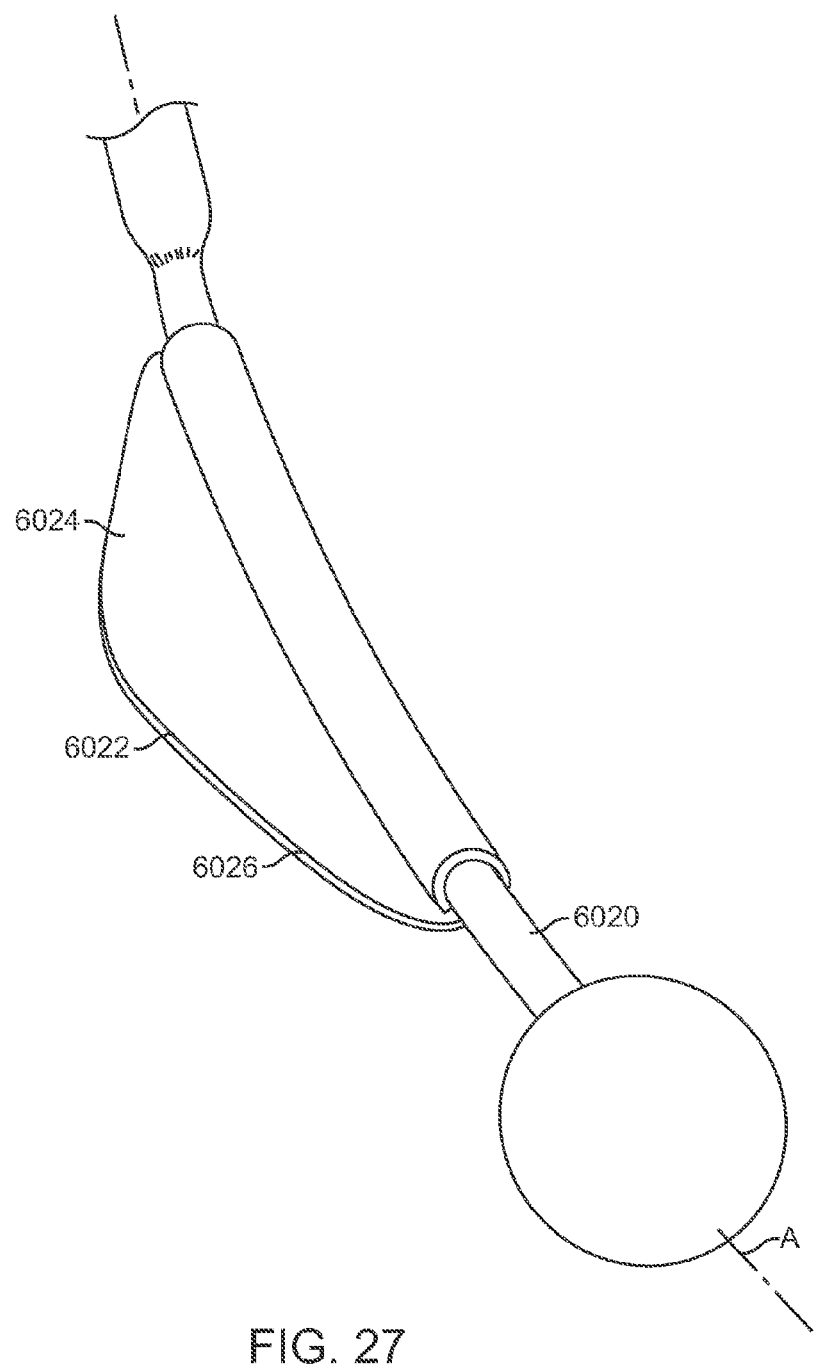
FIG. 27 shows a flap extending laterally from the elongate device so that the flap increases the bearing area.

FIG. 27 shows a simple addition that may be added to a shaft 6020 of one or more of the implant devices described above. A flap 6022 extends laterally from the axis A extending along shaft 6020 of the elongate device so that a major surface 6024 of the flap increases the bearing area near the ends of the device or all along the device, with the flap optionally being rolled or curved inside a surrounding delivery device before deployment. The flap can include plastic, metal, Teflon, or other resiliently deformable sheet materials. The flap may be welded, glued, or mechanically grip the wire of the device. The shape will allow the flap to be easily rolled back up during recapture (with a lateral protrusion of the flap having a ramping tapered shape 6026 such that pulling the proximal ball end into the delivery catheter lumen decreases a lateral profile of the flap).

Figure 28:
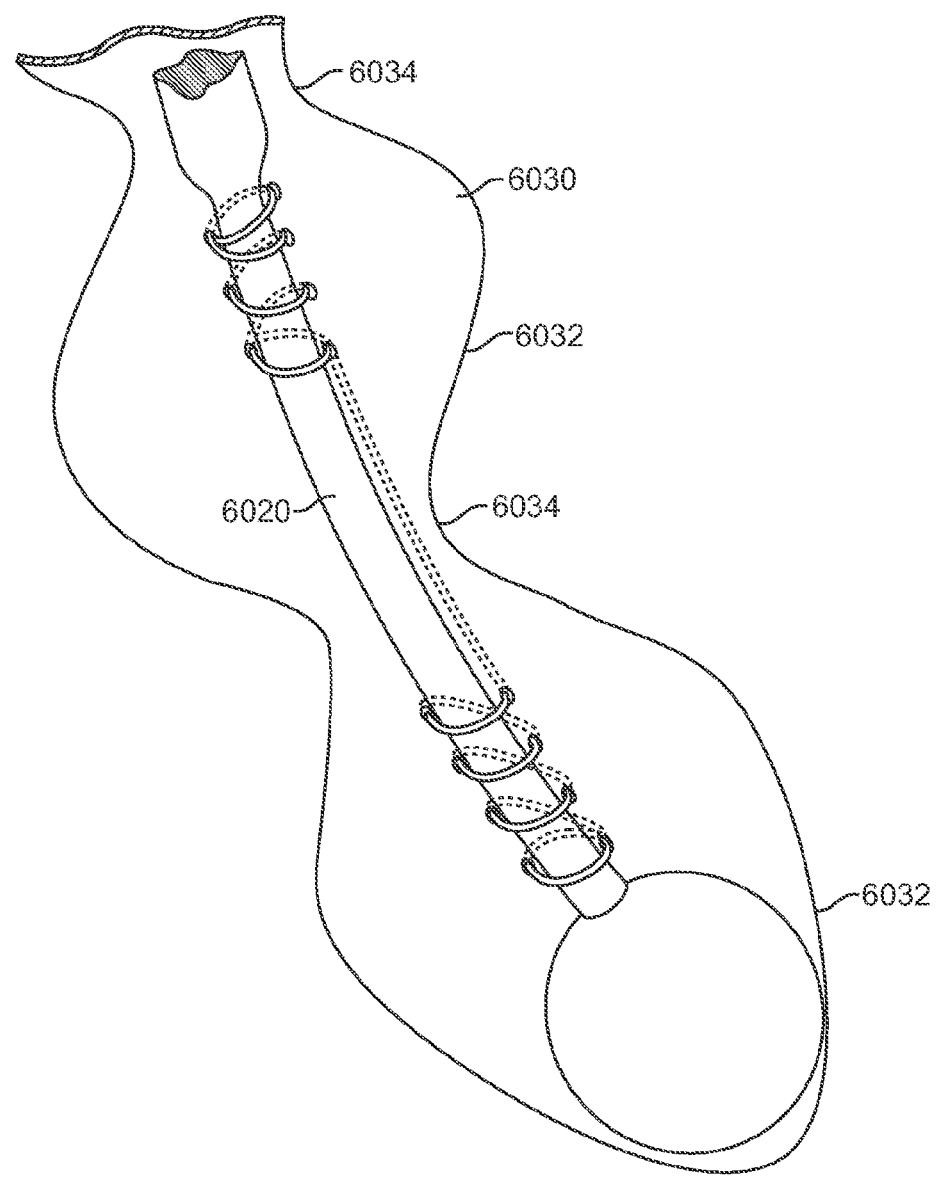
FIG. 28 shows an elongate thin plate body that can unroll so as to extend laterally from its axis (and/or from a wire of the device) so as present an enlarged major surface.

FIG. 28 shows a metal or polymer addition that may be sewed to a shaft 6020 of any of the implants described above, or to other intra-airway lung compression device so as to enhance long-term stability. An elongate thin plate body 6030 can be rolled or curved longitudinally along its length in a small-profile deliverable configuration so as to facilitate constraining the implant within a lumen of a delivery catheter, and can unroll when released so as to extend laterally from the shaft axis (and/or from a wire of the device) so as to present an enlarged major tissue bearing surface in a deployed configuration. The shape of the plate may include one or more protrusions defining at least one taper 6032 (or an axial series of tapers 6032) to facilitate recapture of the plate into a sheath, and necking regions 6034 to allow for implant flexibility along its axis, as axial bending of the implant for lung compression may otherwise be inhibited along the protrusions. The plate may be welded, glued, or sewn to the wire (as shown). Sewing may be performed by knotting the loops, using a continuous stitch or by using a series of hitch knots that can be untied by pulling a thread end. A hitch knot configuration may help decouple the plate from the wire to facilitate removal implant as two separate parts. The thread, line, suture, and/or tether may comprise a metal wire, medical suture, polymer or other suitable material. The plate may be more tightly tied to a smaller wire section of adjacent a proximal device end so that it cannot be easily pushed distally during recapture with the delivery catheter.

Figures 29, 30:
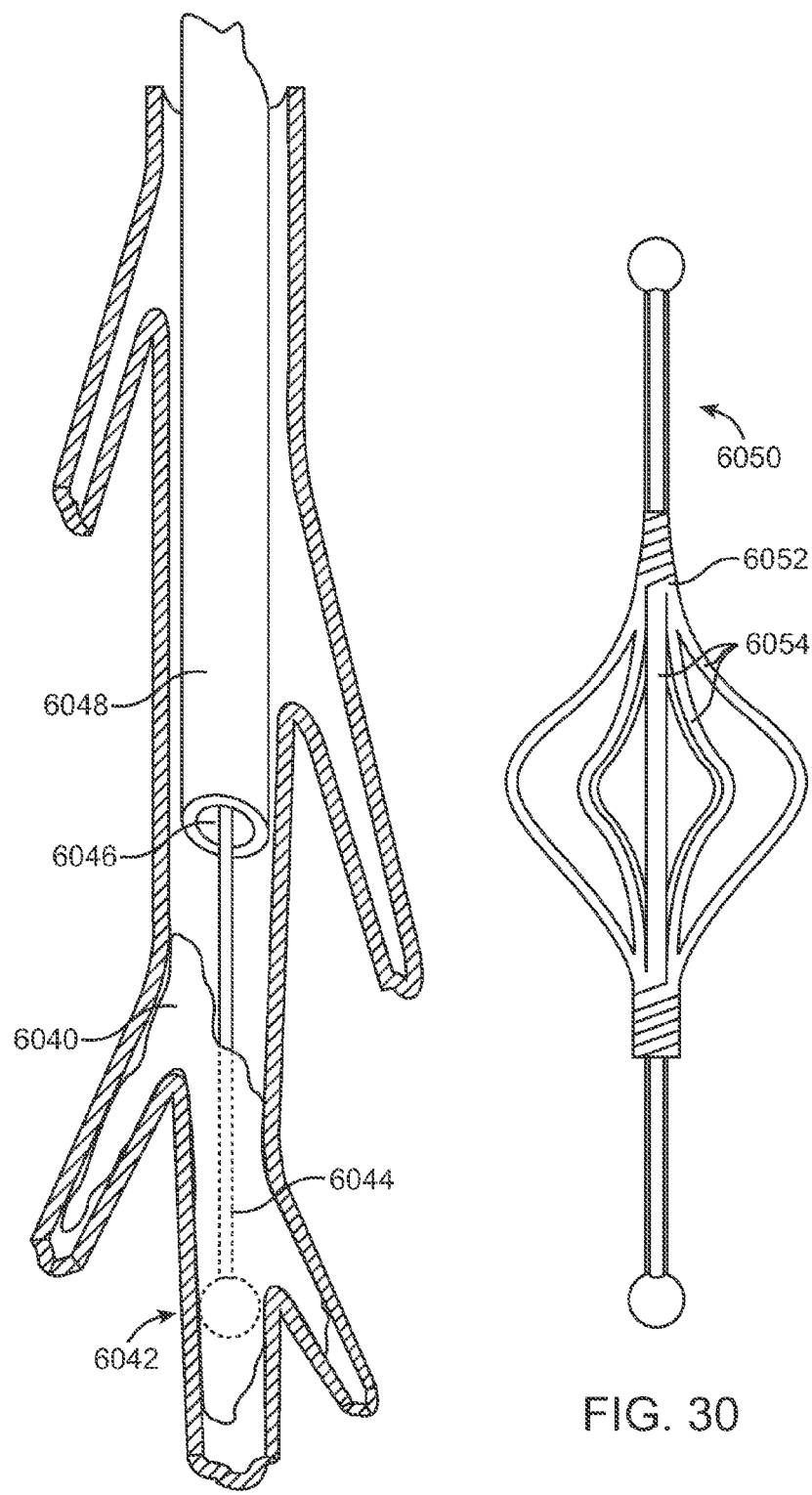
FIG. 29 shows an adhesive injected after deployment of at least a distal portion of the implant.
FIG. 30 shows an implant having an elongate structure separated into elongate portions.

FIG. 29 shows an adhesive 6040 such as a PneuSeal™ adhesive injected into an airway 6042 before, during, and/or after deployment of at least a distal portion 6044 of the implant. The adhesive (or other infusible material) will preferably thicken or set-up in the lung. Along with an appropriate adhesive, simple fillers, sealants, or other materials that can flow into airways to reinforce the tissue (optionally via a tissue reaction to the material) or add additional bearing area to support the coil end, end portion, or the complete implant might be used. The adhesive may be advanced within a lumen 6046 of the delivery catheter 6048 that constrains and delivers the implant, through a smaller adhesive delivery catheter that can be advanced outside of the delivery catheter or through the lumen of the delivery catheter, through an annular space between the delivery catheter and a surrounding sheath, through a second eccentric lumen of the delivery catheter, or the like. Exemplary tissue adhesive compositions and methods for their use are described in U.S. patent Ser. No. 12/602,468, and Ser. No. 12/342,657, filed on Nov. 30, 2009 and Dec. 23, 2008, respectively, the full disclosures of which are incorporated herein by reference.

FIG. 30 shows an implant 6050 having an elongate structure 6052 that is cut from tubing or can otherwise be separated into elongate portions 6054 or struts. The elongate portions 6054 can be biased to be bent separately away from each other and the structure biased to contract axially to shorten while expanding in diameter upon deployment in the airway. This implant may tent or open up the airway to be supported by a greater area of tissue even if the actual area of metal contacting the airway is not much greater than a single wire device. In other words, by interacting with more overall tissue area, the bearing area is effectively enhanced. This implant and/or add-on structure 6052 may be cut from tubing using a laser, water jet, machined or using other methods to make a continuous cut through the length of the tube. This allows the radially expandable structure to be threaded onto a central coil or wire after processing the main coil or wire component. The ends of the expandable member can be cut into a helix that terminates into corresponding cuts on the main body. The distal end may comprise a spring that is threaded on the central coil or wire to be held centrally coaxially with the wire, and may slide over the wire to allow shortening and diameter expansion. The proximal end can be shaped or bent to a smaller diameter to make it grip the coil wire so it does not slide and resist recapture. The central wire can be coated or gripped with a protective shrink tubing polymer surface so the metal components cannot rub and fret or damage an anti-corrosive metal oxide layers on the metal surface.

Figure 31A:
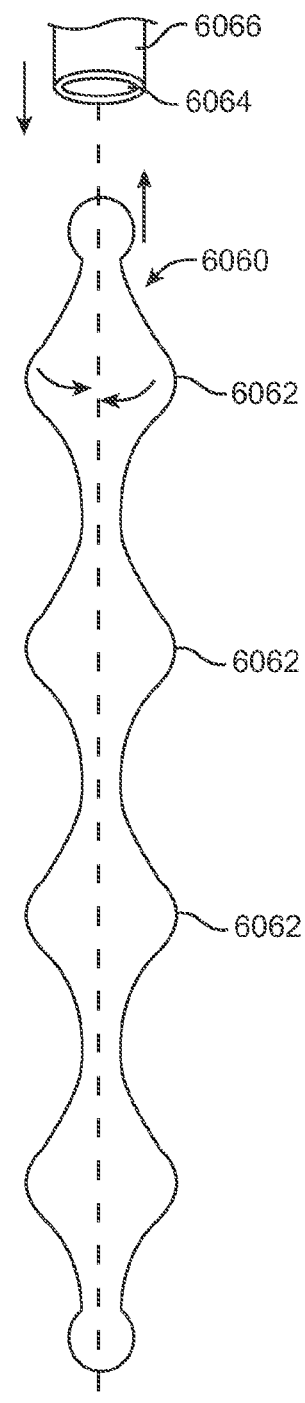
FIGS. 31A and 31B show an implant with an additional component that has winglets to spread the lateral tissue compression load and to axially grab tissue as the device is deployed.
Figure 31B:
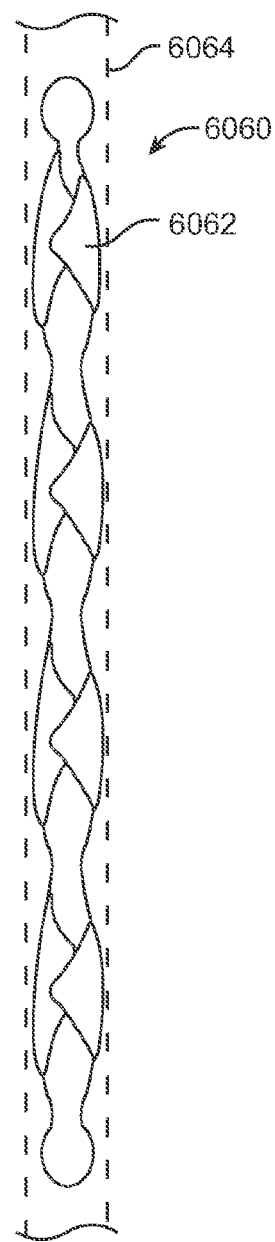

FIG. 31A shows an implant 6060 with an additional component in the form of a sheet or plate of material that has protrusions or winglets 6062 to spread the lateral tissue compression load and to axially grab tissue as the device is deployed. FIG. 31B shows the implant of FIG. 31A folded up in a delivery or recaptured state, such as by advancing implant 6060 into a lumen 6064 of a delivery catheter 6066, with ramped or tapered surfaces of the winglets promoting rolling of the winglets 6062 as described above. The implant may comprise a plate or ribbon material that is shaped as shown, and in which the plate material imposes the desired lung compression forces. In other words, this implant can comprise a single part with balls formed at the ends or it can be a composite of two parts, including a wire and plate as described above.

Figure 32:
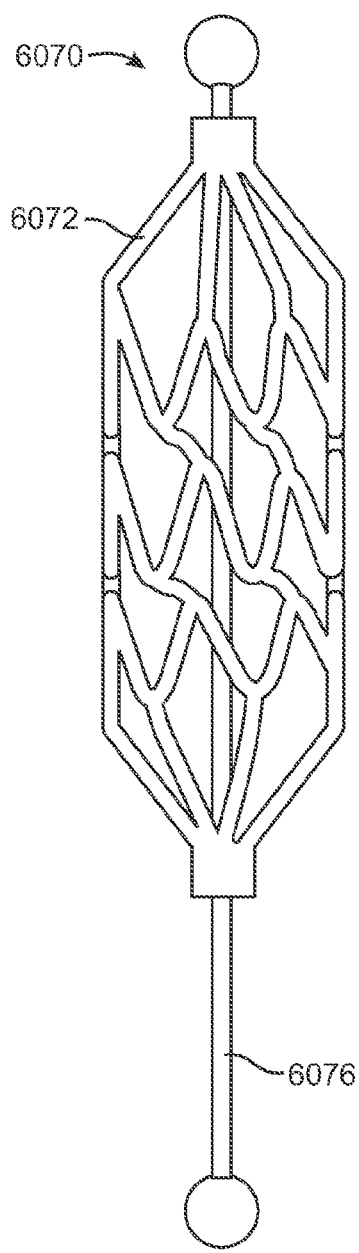
FIG. 32 shows an expanded metal structure similar to that of a vascular stent affixed onto a wire of an implant.

FIG. 32 shows an implant 6070 having an expanded metal structure 6072 similar to that of a vascular stent, in which the end of the expandable structure is affixed onto a wire or shaft 6076 of an implant similar to one of those described above.

The radially expandable structure 6072 may be formed by cutting a tube to define struts, by The length of the expandable structure 6072 may shorten or expand during deployment when diameter expansion occurs. By including long struts at the ends and a pattern with no open terminations, the pattern may be recaptured. A wide variety of stent patterns will may be suitable for use as the expandable structure so as to gain bearing area during deployment, with many embodiments self-expanding radially when the implant is released from the delivery catheter. Each end may be fixed to the coil or one or both ends may be free to slide along the wire.

Figure 33:
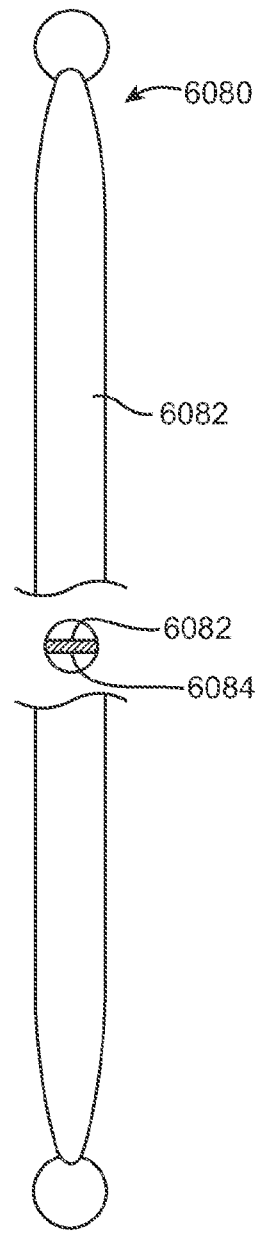
FIG. 33 shows an implant with an elongate element comprising a ribbon.

FIG. 33 shows an implant 6080 with an elongate element comprising a ribbon. The cross section is pictured in the cut out section view, and the orientation the two opposed major surfaces 6082, 6084 may correspond to the axial bends of the device so that one or both of the major surfaces (rather than an edge between the major surfaces) engages the lumen wall so as to urges the lumen wall to bend and locally compress lung tissue.

Figures 34, 35:
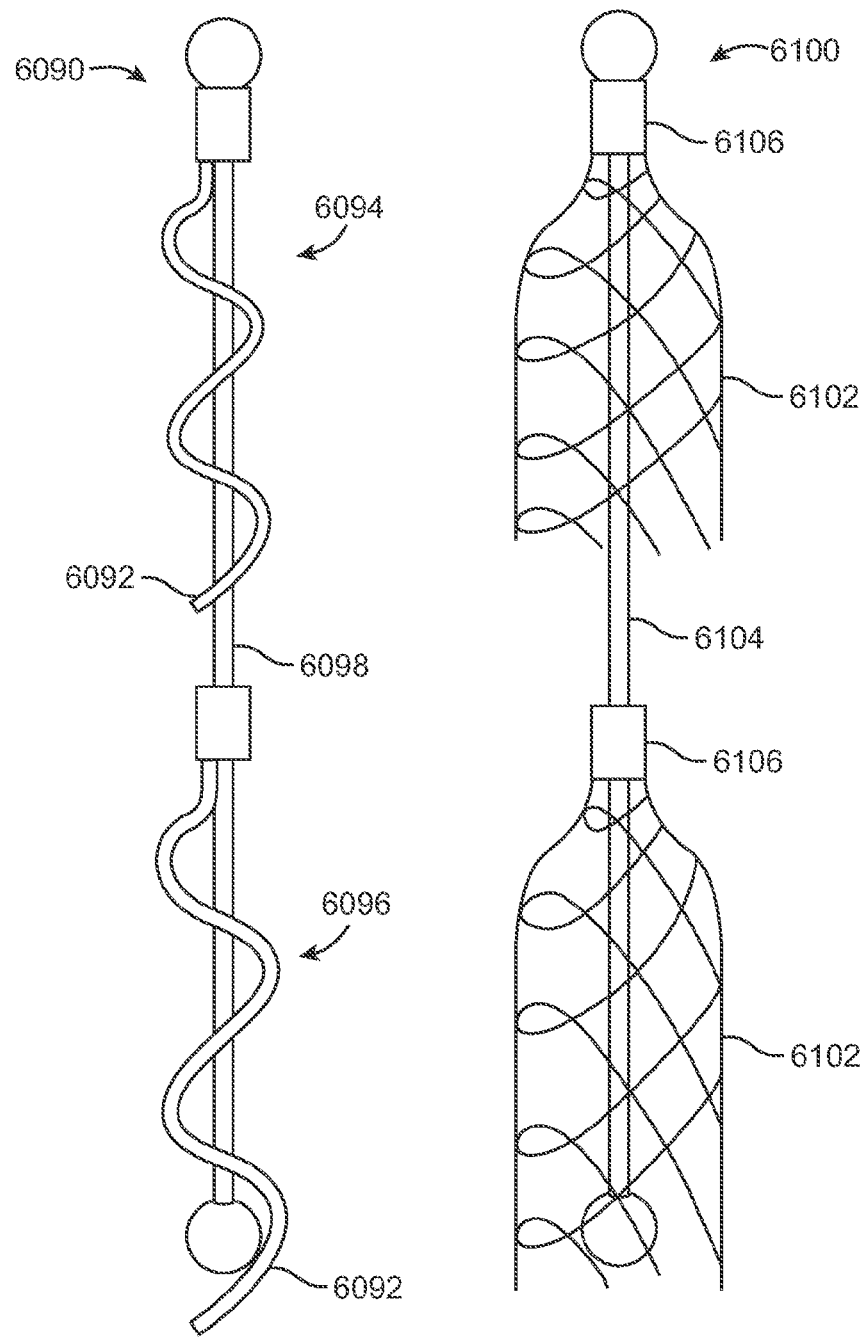
FIG. 34 shows a curved shaped wire attached to the distal and proximal ends of the elongate primary wire or coil of the implant.
FIG. 35 shows a braided structure that expands in diameter as it is deployed attached to the primary structure of the implant.

FIG. 34 shows an implant 6090 having curved shaped wires 6092 that are attached to the distal and proximal portions 6094, 6096 of the elongate primary wire 6098 or coil of the implant. There may be one, two or many such wires that can be glued, welded, crimped, coil bound, sutured, gripped with shrink tubing or otherwise connected to the primary elongate implant structure. As with many of the embodiments described herein, the implant expands laterally so as to enhance an effective bearing area of the implant when the implant is released from the delivery catheter.

FIG. 35 shows an implant 6100 having a plurality of braided structures 6102 that expand in diameter as the implant is deployed. This tents the tissue area to better support the tissue. One two or many of these may be attached to the primary structure or shaft 6104 of the implant. These braids are attached at the proximal end 6106 of the braid to facilitate recapture into the delivery catheter but both ends or the distal ends of the braids may serve as the attachment locations.

Figure 36:
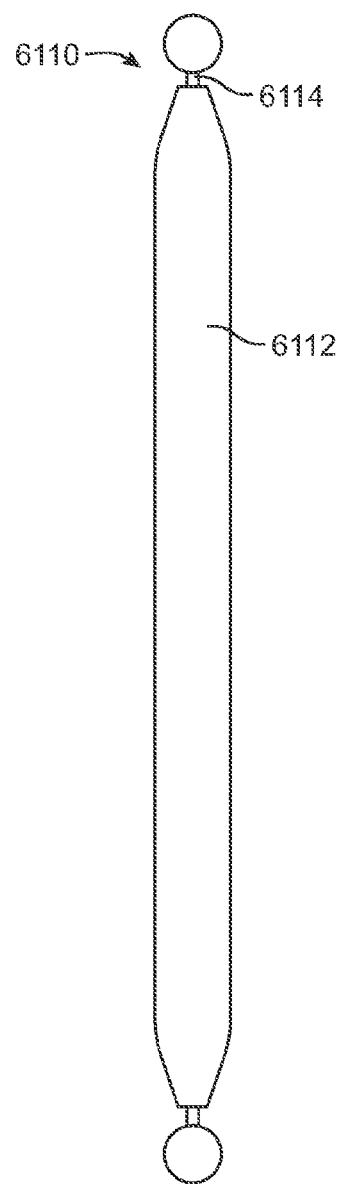
FIGS. 36 and 37 show implants having a sleeve, optionally a hydro gel sleeve, and plugs, optionally hydrogel plugs, that placed on the primary elongate structure.
Figure 37:
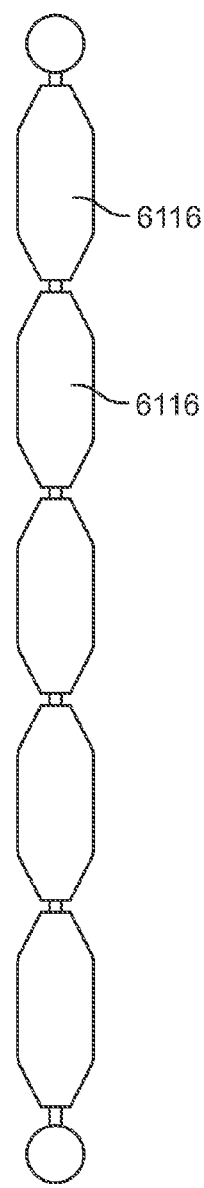

FIG. 36 shows an implant 6110 having a hydrogel sleeve or plug 6112 that is placed on the primary elongate structure 6114. FIG. 37 shows a series of plugs 6116 that are placed on the coil. Because these are short with gaps between them, these plugs may be made of expandable polymers or more rigid materials such as hydrophilic polymers (optionally including PCU), ceramics, metals etc., and the device will still be able to flex appropriately along its axial length during deployment.

Figure 38:
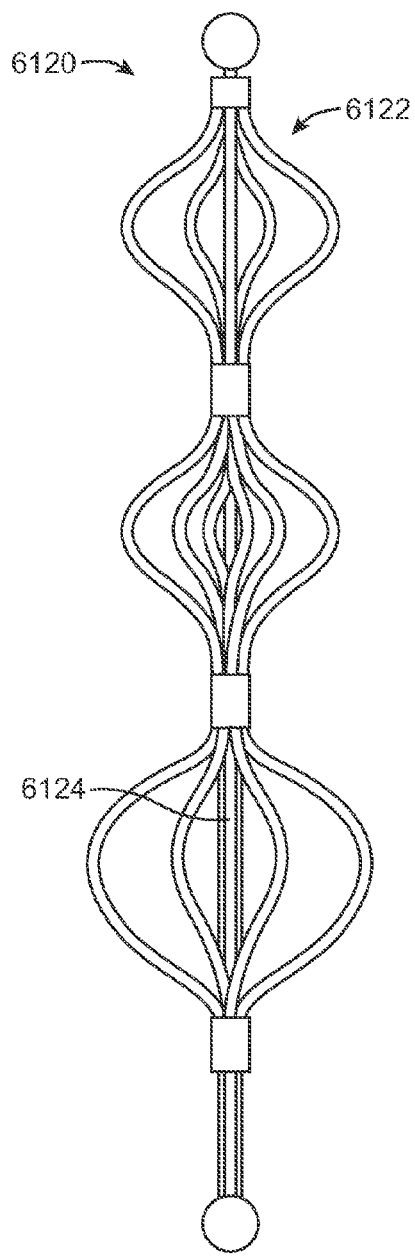
FIG. 38 shows an expandable structure made from a bundle of ribbons, round wires, polymer strands, fibers etc.
Figure 39:
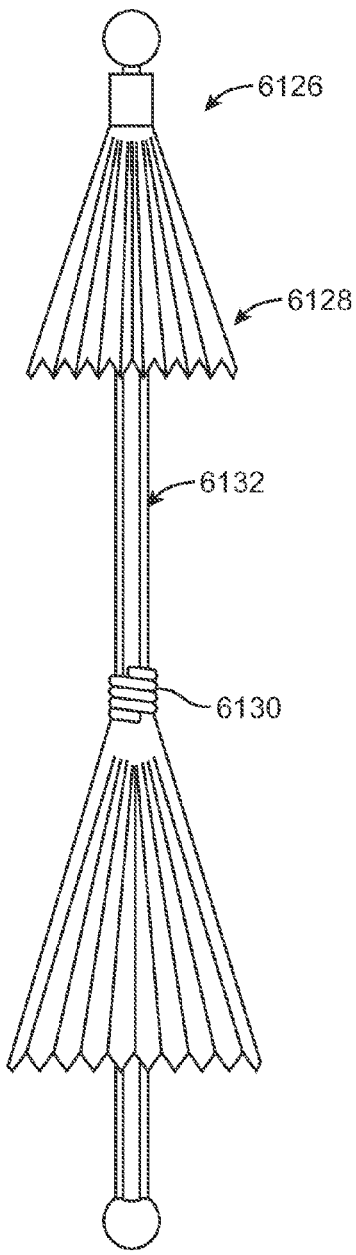
FIG. 39 shows a corrugated polymer or thin metal sheet attached to the primary implant structure.

FIG. 38 shows an implant 6120 having a laterally expandable structure 6122 made from a bundle of ribbons, round wires, polymer strands, fibers, and/or the like. These elements are crimped or connected to the primary implant structure 6124 using any of the methods discussed above. The strands may fold down to be loaded into the delivery catheter, or some or all of a series of expandable regions may slide to change length and allow diameter collapse. FIG. 39 shows an implant 6126 having a polymer or thin metal sheet 6128 that is corrugated to allow it to be compressed into a delivery catheter. A coil spring 6130 is shown gripping on of the structures to hold it to the primary implant structure or shaft 6132. One, two or many of these expandable structures may be provided.

Figure 40:
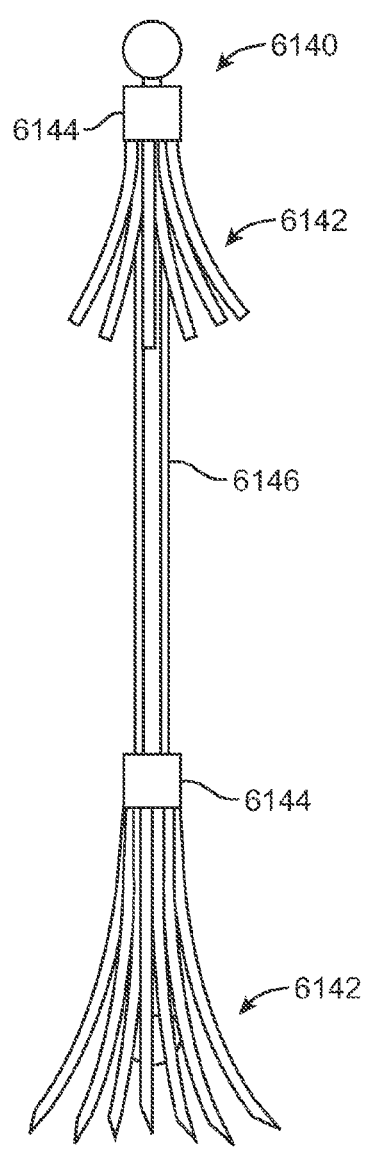
FIG. 40 shows a bundle of strands that are attach only at one end.
Figure 41:
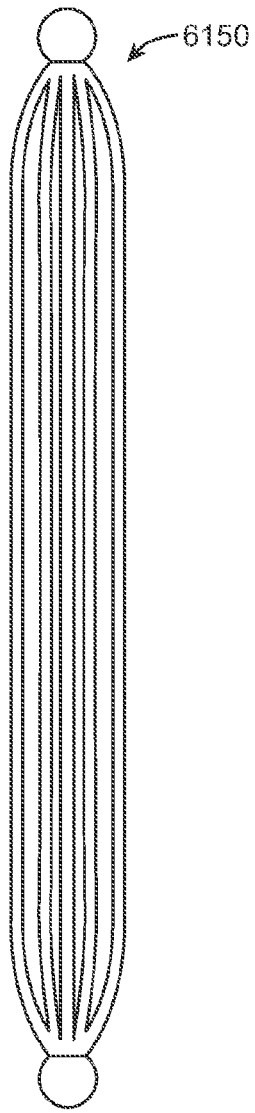
FIG. 41 shows a bundle of wires, ribbons or fibers that are joined at each end of the implant with an integrated ball that is formed from the elements of the bundle.

FIG. 40 shows an implant 6140 having a bundle of strands 6142 that are attach only at one end 6144. These may be attached at the proximal or distal end of the bundle and one, two or several bundles may be attached to a primary device structure 6146. FIG. 41 shows a bundle of wires, ribbons or fibers 6148 that are joined at each end of the implant 6150 with an integrated ball that is formed from the elements of the bundle. By spreading the bundle out laterally (as shown), more tissue may be supported by the device than by a single round wire structure.

Figure 42:
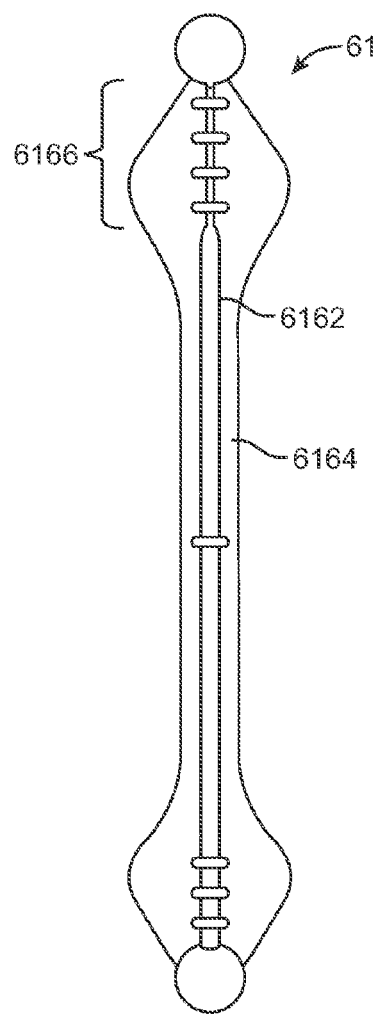
FIGS. 42 and 43 show a implant having a wire with a Teflon or other polymer or metal backer or plate.
Figure 43:
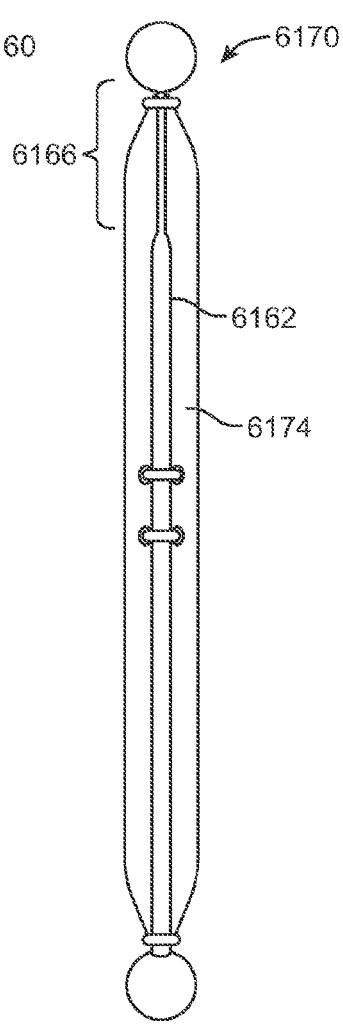
Figure 44:
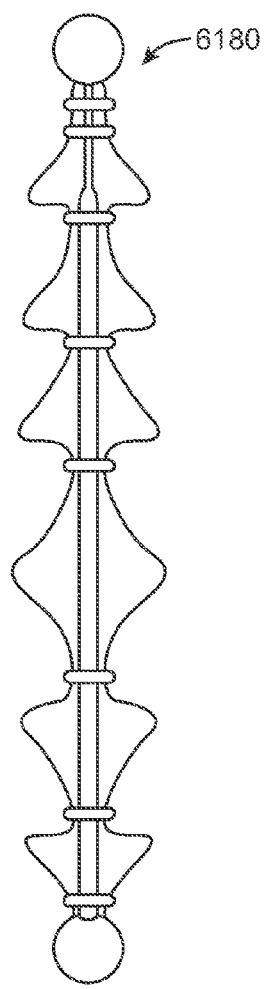
FIG. 44 shows abruptly wide sections that appear as teeth that grip the airway to prevent the device from sliding longitudinally along the airway as it is delivered.

FIGS. 42 and 43 show implants 6160, 6170 having a wire 6162 (for example, as described above regarding FIG. 10). Each implant 6160, 6170 also has an associated Teflon or other polymer or metal backer or plate 6164, 6174 that is attached using suture or other attachment techniques described above. A proximal portion 6166 with a locally reduced wire diameter near the proximal end is tied more tightly to the backer to inhibit relative axial sliding between the backer and wire (and particularly to prevent the backer from sliding in the distal direction) during recapture. The backer may optionally include a material that can swell, soften or stiffen with time. The ideal backer may be broad and may be folded or rolled to fit into a delivery catheter. Sections or local regions of the backer may be narrow to enhance lung tissue-compressing axial bending of the implant during deployment, with other sections being thicker or wider to provide more bearing area. FIG. 44 shows an implant 6180 having abruptly wide protrusions or sections that appear as teeth that grip the airway to prevent the device from sliding longitudinally along the airway as it is delivered. Prevention of slippage in this way may increase the ability of the device to draw the airway into a small volume so as to compress diseased lung tissue. Coatings may be applied to enhance biocompatibility, reduce friction, allow for the delivery of drugs over time, and provide a porosity or texture that reduces the propensity of inflaming tissue.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims presented will define the scope of the invention and that methods and structures within the scope of these claims and their equivalents be covered thereby.

What is claimed is:

1. An implant for treating a lung of a patient, the lung including an airway system having an airway, the implant comprising:

an elongate body having a proximal end and a distal end defining an axis therebetween;

the elongate body having a delivery configuration and a deployed configuration, the elongate body in the delivery configuration having a lateral bearing surface in an unexpanded configuration about the elongate body, the axis of the elongate body in the delivery configuration being sufficiently straight for advancement distally into the airway system;

the elongate body being deployable from the delivery configuration to the deployed configuration within the airway system such that the lateral bearing surface of the implant expands laterally from the axis of the elongate body to an expanded configuration to increase the lateral bearing surface, deployment of the elongate body within the airway effecting bending of the elongate body so that the lateral bearing surface bears laterally against a luminal surface of the airway from within the airway system sufficiently to bend the airway while the expanded lateral bearing surface of the implant inhibits penetration of the implant through the airway, and sufficient that local compression of lung tissue enhances tension in other lung tissue of the patient sufficiently to enhance lung function of the patient.

2. The implant of claim 1, wherein deploying the elongate body within the airway system comprises bending the elongate body within the airway so that the elongate body bends a first axial airway region toward a second axial airway region so as to compress the lung tissues between the first and second axial airway regions when the first and second axial airway regions surround a first axial portion of the elongate body and a second axial portion of the elongate body offset along the axis, respectively.

3. A system comprising the implant of claim 1, wherein the lateral expansion of the lateral bearing surface of the elongate body comprises resilient lateral expansion, the system further comprising a delivery catheter having a lumen sized for receiving the implant so that the implant is laterally constrained within the lumen of the delivery catheter during delivery to facilitate advancing of the implant into the airway system, and so that withdrawing the catheter proximally from around the implant deploys the implant within the airway system.

4. The system of claim 3, wherein the elongate body comprises an axially resilient body so that compressing of the lung tissue is effected by resilient bending of the elongate body toward a relaxed configuration, the delivery catheter constraining the axis of the elongate body toward a sufficiently straight configuration to facilitate advancing the implant into the airway system.

5. The system of claim 3, wherein the lateral bearing surface of the elongate body comprises a laterally bent or rolled sheet material when the lateral bearing surface is in the unexpanded configuration and wherein lateral expansion of the lateral bearing surface of the elongate body comprises laterally flattening or unrolling of the sheet material to the expanded configuration, the flattened or unrolled sheet material having first and second opposed major surfaces and the lateral bearing surface comprising at least a portion of the first major surface.

6. The system of claim 3, wherein the lateral expansion of the lateral bearing surface comprises bending of at least one wire or filament from an axial configuration extending along the elongate body of the implant in the delivery configuration, the at least one wire or filament defining the lateral bearing surface and being urgable laterally by the elongate body so as to effect compression of the lung tissue when the implant is released in the airway system.

7. The system of claim 3, wherein the lateral expansion of the lateral bearing surface of the elongate body comprises radial expansion of a radially expandable structure, the elongate body extending axially along the radially expandable structure, the radially expandable structure defining the lateral bearing surface and being urged laterally by the elongate body during deployment so as to effect compression of the lung tissue.

8. The system of claim 7, wherein the radial expansion of the lateral bearing surface comprises lateral separation of struts defined between cuts or slots along a tube, the tube defining the radially expandable structure.

9. The system of claim 7, wherein the radial expansion of the lateral bearing surface comprises radial expansion of a braided sleeve, the braided sleeve defining the radially expandable structure and shortening axially during radial expansion.

10. An implant for treating a lung of a patient, the lung including an airway system having an airway, the implant comprising:
    an implant body having a proximal end, a distal end, and an elongate length defining an axis therebetween, the implant body having a lateral bearing surface transverse to the axis, the implant body having a delivery configuration in which the axis of the implant body is sufficiently straight for axial advancement distally into the airway system; and
    the implant body deployable from the delivery configuration to a deployed configuration within the airway system by axially bending the implant sufficiently that the lateral bearing surface of the implant bends a first axial airway region toward a second axial airway region and compresses lung tissues between the first and second axial airway regions, wherein an interface between the lateral bearing surface of the deployed implant and the airway is hydrophilic and/or locally expanded along the axis of the implant so as to inhibit damage to the airway during long-term implantation.

11. A system comprising the implant of claim 10, the system further comprising an adhesive delivery device in fluid communication with the implant so that an adhesive is deliverable with the implant such that the adhesive inhibits penetration of the implant through an airway wall.

12. The implant of claim 10, wherein the implant comprises an axial series of plugs or lateral protrusions, wherein the implant body bends between the plugs or protrusions and wherein the plugs or protrusions locally inhibit penetration of the implant through an airway wall.

13. The implant of claim 10, wherein the lateral bearing surface of the implant comprises a polymer material, the polymer material sufficiently hydrophilic for biofilm formation inhibition when the implant is disposed in the lung.

14. The implant of claim 13, wherein the implant body comprises a resilient metal shaft disposed within a sleeve of the polymer material, the sleeve comprising a poly carbonate urethane (PCU).

15. A lung volume reduction system comprising:
    an implantable device that imparts a compression force on lung tissue, wherein the implant comprises an elongate implantable ribbon element having first and second opposed major surfaces and edges between the first and second opposed major surfaces, the elongate implantable ribbon element being deployable from a first configuration to a second configuration, the elongate ribbon element in the first configuration extending along an axis of the elongate ribbon sufficiently for axial insertion into an airway system of the lung tissue, the inserted elongate ribbon element deployable to the second configuration where a first implant portion of the implant engages a first airway axial region of an airway system and a second implant portion of the implant engages a second airway axial region of the airway system, the implant urging the first airway axial region and the second airway axial region toward each other thereby compressing a volume of lung tissue disposed between the first airway axial region and the second airway axial region when the inserted elongate ribbon element is deployed to the second configuration.

16. The lung volume reduction system of claim 15, wherein the implant further comprises a proximal end extending from the elongate implantable ribbon element, and wherein the proximal end is not driven into the lung tissue upon implantation of the elongate implantable ribbon element, so as to facilitate recapture of the implanted elongate implantable ribbon element.

17. The lung volume reduction system of claim 15, wherein the implant further comprises a covering disposed over at least a portion of the elongate implantable ribbon element.

18. The lung volume reduction system of claim 15, wherein an orientation of the first and second opposed major surfaces correspond to an axial bend along the elongate implantable ribbon element.

19. The lung volume reduction system of claim 15, wherein the edges between the first and second opposed major surfaces do not engage the airway system to locally compress tissue.

* * * * *